United States Patent
Matthews et al.

(10) Patent No.: US 7,168,429 B2
(45) Date of Patent: Jan. 30, 2007

(54) AUTO-TITRATION PRESSURE SUPPORT SYSTEM AND METHOD OF USING SAME

(75) Inventors: Greg Matthews, Plum, PA (US); Michael T. Kane, Harrison City, PA (US); Winslow K. Duff, Export, PA (US); Rochelle Eisert, Pittsburgh, PA (US); Daniel Martin, Delmont, PA (US)

(73) Assignee: RIC Investments, LLC, Wilmington, DE (US)

( * ) Notice: Subject to any disclaimer, the term of this patent is extended or adjusted under 35 U.S.C. 154(b) by 284 days.

(21) Appl. No.: 10/268,406

(22) Filed: Oct. 10, 2002

(65) Prior Publication Data

US 2003/0111079 A1 Jun. 19, 2003

Related U.S. Application Data

(60) Provisional application No. 60/331,838, filed on Nov. 20, 2001, provisional application No. 60/329,250, filed on Oct. 12, 2001.

(51) Int. Cl.
*A61M 16/00* (2006.01)
*A62B 7/00* (2006.01)

(52) U.S. Cl. ............... 128/204.21; 128/204.22; 128/204.23; 128/204.26

(58) Field of Classification Search ........... 128/204.18, 128/204.21, 204.22, 204.23, 204.26, 848
See application file for complete search history.

(56) References Cited

U.S. PATENT DOCUMENTS

| | | | |
|---|---|---|---|
| 5,148,802 A | 9/1992 | Sanders et al. | |
| 5,245,995 A | 9/1993 | Sullivan et al. | |
| 5,259,373 A | 11/1993 | Gruenke et al. | |
| 5,313,937 A | 5/1994 | Zdrojkowski | |
| 5,335,654 A | 8/1994 | Raporport | |
| 5,458,137 A | 10/1995 | Axe et al. | |
| 5,490,502 A | 2/1996 | Rapoport et al. | |
| 5,492,113 A | 2/1996 | Estes et al. | |
| 5,503,146 A * | 4/1996 | Froehlich et al. | 128/204.23 |
| 5,535,739 A | 7/1996 | Rapoport et al. | |
| 5,549,106 A | 8/1996 | Gruenke et al. | |
| 5,551,418 A | 9/1996 | Estes et al. | |
| 5,632,269 A | 5/1997 | Zdrojkowski | |
| 5,645,053 A * | 7/1997 | Remmers et al. | 128/204.23 |
| 5,682,878 A | 11/1997 | Ogden | |
| 5,685,296 A | 11/1997 | Zdrojkowski et al. | |

(Continued)

FOREIGN PATENT DOCUMENTS

WO    WO 00/76389 A2    12/2000

(Continued)

*Primary Examiner*—Michael J. Hayes
*Assistant Examiner*—Michael Mendoza
(74) *Attorney, Agent, or Firm*—Michael W. Haas

(57) ABSTRACT

A pressure support system and method of treating disordered breathing that optimizes the pressure delivered to the patient to treat the disordered breathing while minimizing the delivered pressure for patient comfort. The controller in the pressure support system operates as a set of prioritized control layers, wherein each control layer competes for control of the pressure generating system to implement a unique pressure control process. The pressure support system also controls the pressure provided to the patient based on the variability of the monitored data and a trend analysis of this data, including an indication of the skewness of the patient's inspiratory waveform.

18 Claims, 21 Drawing Sheets

U.S. PATENT DOCUMENTS

| | | | |
|---|---|---|---|
| 5,704,345 A | 1/1998 | Berthon-Jones | |
| 5,794,615 A | 8/1998 | Estes | |
| 5,809,065 A | 9/1998 | Dapper et al. | |
| 5,823,187 A | 10/1998 | Estes et al. | |
| 5,845,636 A | 12/1998 | Gruenke et al. | |
| 5,901,704 A | 5/1999 | Estes et al. | |
| 5,904,141 A | 5/1999 | Estes et al. | |
| 6,029,664 A | 2/2000 | Zdrojkowski et al. | |
| 6,029,665 A | 2/2000 | Berthon-Jones | |
| 6,085,747 A | 7/2000 | Axe et al. | |
| 6,099,481 A | 8/2000 | Daniels et al. | |
| 6,105,575 A | 8/2000 | Estes et al. | |
| 6,138,675 A | 10/2000 | Berthon-Jones | |
| 6,360,741 B2 | 3/2002 | Truschel | |
| 6,450,164 B1 * | 9/2002 | Banner et al. | 128/204.21 |
| 6,484,719 B1 * | 11/2002 | Berthon-Jones | 128/204.23 |
| 6,626,175 B2 * | 9/2003 | Jafari et al. | 128/204.21 |
| 6,814,074 B1 * | 11/2004 | Nadjafizadeh et al. | 128/204.23 |

FOREIGN PATENT DOCUMENTS

| | | |
|---|---|---|
| WO | WO 00/78379 A1 | 12/2000 |
| WO | WO 01/32069 A2 | 5/2001 |
| WO | WO 02/18002 | 3/2002 |
| WO | WO 02/28460 A1 | 4/2002 |

* cited by examiner

AUTO-TITRATION PRESSURE SUPPORT SYSTEM AND METHOD OF USING SAME

CROSS-REFRENCE TO RELATED APPLICATIONS

This application claims priority under 35 U.S.C. § 119(e) from U.S. provisional patent application No. 60/329,250 filed Oct. 12, 2001 and U.S. provisional patent application No. 60/331,838 filed Nov. 20, 2001 the contents of which are incorporated herein by reference.

BACKGROUND OF THE INVENTION

1. Field of the Invention

The present invention pertains to a pressure support system and method of treating disordered breathing, and, in particular, to an auto-titration pressure support system and to a method of automatically titrating a pressure support system to optimize the pressure delivered to the patient to treat the disordered breathing while otherwise minimizing the delivered pressure for patient comfort.

2. Description of the Related Art

It is well known that many individuals suffer from disordered breathing during sleep. Obstructive sleep apnea (OSA) is a common example of such disordered breathing suffered by millions of people through the world. OSA is a condition in which sleep is repeatedly interrupted by an inability to breathe, which occurs due to an obstruction of the airway; typically the upper airway or pharyngeal area. Obstruction of the airway is generally believed to be due, at least in part, to a general relaxation of the muscles which stabilize the upper airway segment, thereby allowing the tissues to collapse the airway.

Those afflicted with OSA experience sleep fragmentation and complete or nearly complete cessation of ventilation intermittently during sleep with potentially severe degrees of oxyhemoglobin desaturation. These symptoms may be translated clinically into extreme daytime sleepiness, cardiac arrhythmias, pulmonary-artery hypertension, congestive heart failure and/or cognitive dysfunction. Other consequences of OSA include right ventricular dysfunction, carbon dioxide retention during wakefulness, as well as during sleep, and continuous reduced arterial oxygen tension. Sleep apnea sufferers may be at risk for excessive mortality from these factors as well as by an elevated risk for accidents while driving and/or operating potentially dangerous equipment.

Even if a patient does not suffer from a complete obstruction of the airway, it is also known that adverse effects, such as arousals from sleep, can occur where there is only a partial obstruction of the airway. Partial obstruction of the airway typically results in shallow breathing referred to as a hypopnea. Other types of disordered breathing include upper airway resistance syndrome (UARS) and vibration of the airway, such as vibration of the pharyngeal wall, commonly referred to as snoring. It is also known that snoring can accompany closure of the airway leading to UARS, hypopnea, or apnea. Thus, snoring serves as an indicator that the patient is experiencing abnormal breathing.

It is known to treat such disordered breathing by applying a continuous positive air pressure (CPAP) to the patient's airway. This positive pressure effectively "splints" the airway, thereby maintaining an open passage to the lungs. It is also known to provide a positive pressure therapy in which the pressure of gas delivered to the patient varies with the patient's breathing cycle, or varies with the patient's effort, to increase the comfort to the patient. This pressure support technique is referred to a bi-level pressure support, in which the inspiratory positive airway pressure (IPAP) is delivered to the patient is higher than the expiratory positive airway pressure (EPAP).

It is further known to provide a positive pressure therapy in which a continuous positive pressure is provided to the patient, and where the level of this pressure is automatically adjusted based on the detected conditions of the patient, such as whether the patient is snoring or experiencing an apnea, hypopnea or upper airway resistance. This pressure support technique is referred to as an auto-titration type of pressure support, because the pressure support device seeks to provide a pressure to the patient that is only as high as necessary to treat the disordered breathing.

Examples of conventional auto-titration pressure support systems are disclosed in U.S. Pat. No. 5,245,995 to Sullivan et al.; U.S. Pat. Nos. 5,259,373; 5,549,106, and 5,845,636 all to Gruenke et al.; U.S. Pat. Nos. 5,458,137 and 6,058,747 both to Axe et al.; U.S. Pat. Nos. 5,704,345; 6,029,665, and 6,138,675 all to Berthon-Jones; U.S. Pat. No. 5,645,053 to Remmers et al.; and U.S. Pat. Nos. 5,335,654; 5,490,502; 5,535,739, and 5,803,066 all to Rapoport et al. All of these conventional pressure support systems, with the possible exception of U.S. Pat. No. 5,645,053 to Remmers et al., are reactive to the patient's monitored condition. That is, once a condition occurs that indicates abnormal breathing, the system alters the pressure support system to treat this condition. The present inventors discovered, however, that this treatment technique may not be suitable for all patients, and may cause the system to unnecessarily react to mild, temporary anomalies.

Furthermore, these auto-titration pressure support systems typically attempt to treat one condition of the patient, such as snoring or a flow limitation in the patient's inspiratory waveform. It is believed that this micro, target treatment, approach, focusing on one or two conditions, fails to provide an adequate treatment for a patient, which, in essence, is a very complicated system, affected by a variety of variables.

In addition, these conventional auto-titration systems present different approaches to detecting a condition of the patient. Each approach attempts to improve the ability to detect conditions of the patient that are truly indicative of a breathing disorder. However, each approach is believed to be limited in its ability to monitor and treat a wide population of patients in a robust manner.

SUMMARY OF THE INVENTION

Accordingly, it is an object of the present invention to provide an auto-titration pressure support system that overcomes the shortcomings of conventional auto-titration systems. This object is achieved according to one embodiment of the present invention by providing an auto-titration pressure support system that includes a pressure generating system adapted to generate a flow of breathing gas at a selectable pressure level, a patient circuit having a first end adapted to be coupled to the pressure generating system and a second end adapted to be coupled to an airway of a patient, a monitoring system associated with the patient circuit or pressure generating system and adapted to measure a parameter indicative of a pressure at a patient's airway and a flow of gas in such a patient's airway and to output a pressure signal and a flow signal indicative thereof, and a controller coupled to the monitoring system and the pressure generating system. The controller controls the pressure generating system based on the output of the monitoring system, and is programmed to operate according to a set of prioritized control layers. Each control layer competes for control of the pressure generating system with the other control layers, and implements a unique pressure control process.

In a further embodiment, the control performs a trend analysis on the output of the monitoring system and controls the pressure generating system according to the results of this trend analysis.

In a still further embodiment, the controller determines a breathing parameter from the output of the monitoring system, and analyzes a variability of the breathing parameter. The controller then controls the pressure generating system based on a result of the variability analysis.

In yet another embodiment, the controller monitors leakage of gas from the patient circuit and reduces a pressure provided to a patient by the pressure generating system for a predetermined period of time responsive to a determination that a rate of the leakage of gas exceeds a predetermined threshold and increases the pressure back to a prior pressure level after the predetermined period of time has elapsed.

In another embodiment of the present invention, the controller determines a skewness of a patient's inspiratory waveforms from the output of the flow sensor and controls the pressure generating system according to the skewness determination.

In a still further embodiment of the present invention, the controller determines whether the patient is experiencing a central apnea/hypopnea or an obstructive/restrictive apnea/hypopnea by monitoring one or more of the following: (1) at least one shape parameter associated with the flow of gas during an apnea/hypopnea period, and (2) a characteristic of the flow of gas at the end of the apnea/hypopnea period indicative of an increase in respiratory effort.

In another embodiment of the present invention, the controller determines whether the patient is experiencing an apnea/hypopnea and determines whether to increase or decrease the pressure as a result of the detection of the apnea/hypopnea based on the current pressure as compared to a pressure treatment limit. The pressure treatment limit is set by the controller based on the pressure at the time the apnea/hypopnea occurred. This feature of the present invention prevents the patient from receiving additional pressure increases if past pressure increases did not solve the condition that caused the apnea/hypopnea, which may be the case if the patient is experiencing a central apnea/hypopnea.

It is yet another object of the present invention to provide a method of delivering a pressure support treatment to a patient according to the pressure support system operating functions discussed above.

These and other objects, features and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF THE PRESENTLY PREFERRED EMBODIMENTS OF THE INVENTION

A. System Hardware

Figure 1:
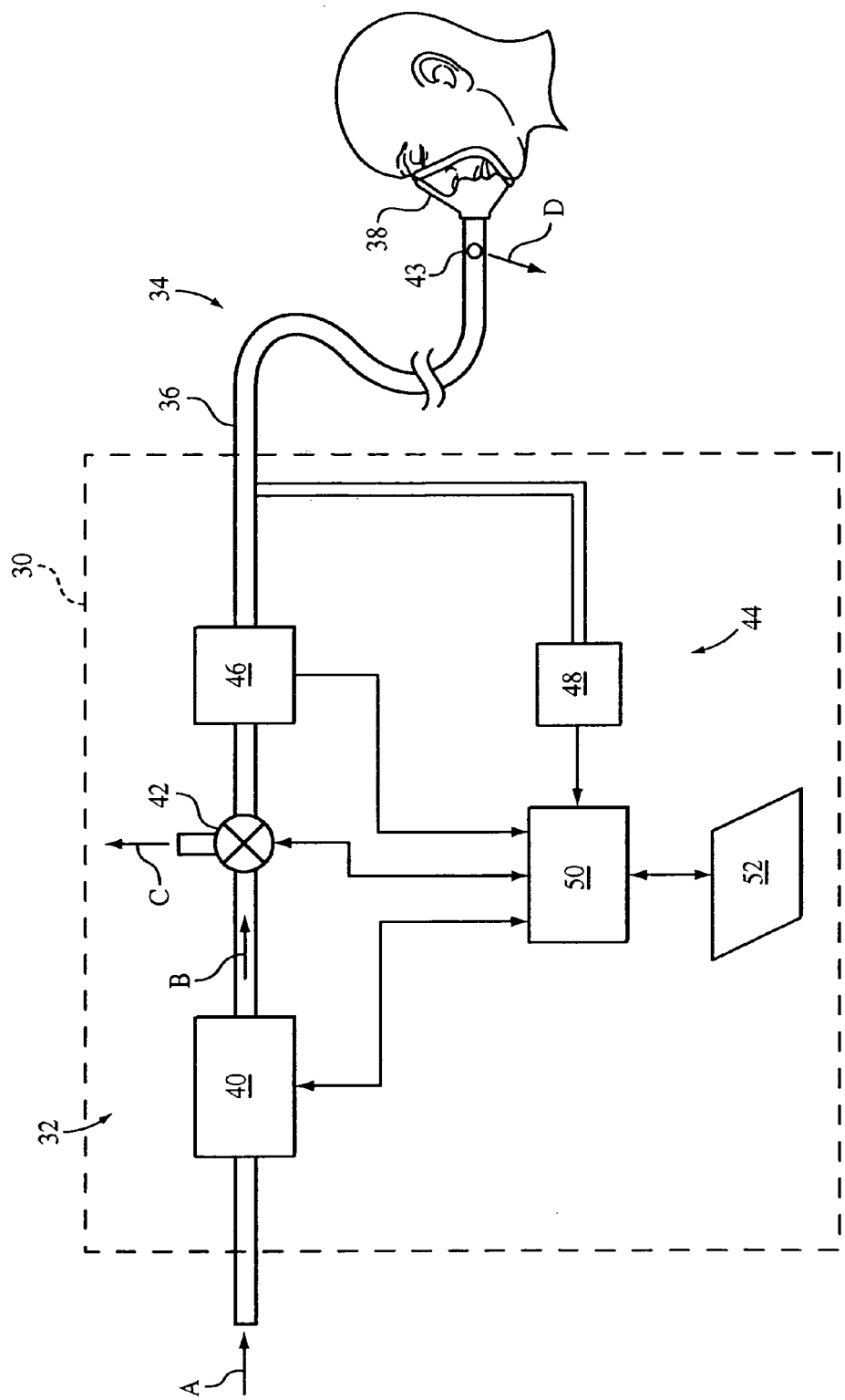
FIG. 1 is a schematic diagram of a pressure support system adapted to operate according to the auto-titration technique of the present invention.

The basic components of a pressure support system 30 that is adapted to implement the auto-titration technique according to the principles of the present invention is discussed below with reference to FIG. 1. Pressure support system 30 includes a pressure generating system, generally indicated at 32, and a patient circuit 34, which includes a conduit 36 and a patient interface device 38. In the illustrated embodiment, pressure generating system 32 includes a pressure generator 40 and a pressure control valve 42 as the outlet of the pressure generator.

Pressure generator 40 receives the breathing gas from a source of breathing gas, as indicated by arrow A, and outputs the breathing gas, as indicated by arrow B, to patient circuit 34 at a pressure that is greater than atmosphere for delivery to the airway of a patient (not shown). In a preferred embodiment of the present invention, pressure generator 40 is a mechanical pressure generator, such as a blower, bellows or piston, that receives ambient air, for example, at an inlet from the gas source. Pressure control valve 42 controls the pressure of the flow of breathing gas delivered to the patient via the patient circuit by restricting the flow to the patient, by diverting flow from patient circuit 34, as indicated by arrow C, or a combination thereof.

The present invention further contemplates controlling the pressure of the flow of breathing gas delivered to the patient by controlling the operating speed of pressure generator 40, either alone or in combination with valve 42. Of course, valve 42 can be eliminated if operating speed alone is used to control the pressure of the flow of breathing gas delivered to the patient. Those skilled in the art can appreciate that other techniques for controlling the pressure of the flow of breathing gas delivered to the patient can be implemented in pressure support system 30, either alone or in combination to those discussed above. For example, a flow restricting valve (not shown) can be provided upstream of pressure generator 40 that controls the flow (arrow A) of gas to pressure generator 40, and, hence, the pressure of the flow of gas output for delivery to the patient.

Typically, the source of breathing gas is the ambient atmosphere, where its pressure is subsequently elevated for delivery to the patient by the pressure generating system. It is to be understood, that other sources of breathing gas are contemplated by the present invention, such as oxygen or an oxygen mixture from an oxygen source. It is to be further understood, that the present invention contemplates that pressurized air can be provided to the airway of the patient directly from a tank of pressurized air via the patient circuit without using a pressure generator, such as a blower, bellows or piston, to increase the pressure of the air. Of course, a pressure regulator, such as valve 42 would be required to control the pressure of the gas delivered to the patient. The important feature with respect to the present invention is that pressurized breathing gas is provided in the patient circuit for delivery to the patient, not necessarily the source or manner in which the pressurized breathing gas is generated.

Although not shown in FIG. 1, the present invention also contemplates providing a secondary flow of gas, either alone or in combination with the primary flow of gas (arrow A) from atmosphere. For example, a flow of oxygen from any suitable source can be provided upstream to pressure generator 40 or downstream of the pressure generator in the patient circuit or at the patient interface device to control the fraction of inspired oxygen delivered to the patient.

In the illustrated embodiment, conduit 36 in patient circuit 34 has one end coupled to the output of the pressure generator 40 and another end coupled to patient interface device 38. Conduit 36 is any tubing capable of carrying the gas flow from the pressure generator to the airway of the patient. Typically, a distal portion of the conduit 36 relative to pressure generator 40 is flexible to allow for freedom of movement of the patient. It is to be understood that various components may be provided in or coupled to patient circuit 34. For example, a bacteria filter, pressure control valve, flow control valve, sensor, meter, pressure filter, humidifier and/or heater can be provided in or attached to the patient circuit. Likewise, other components, such as mufflers and filters can be provided at the inlet of pressure generator 40 and at the outlet of valve 42.

Patient interface device 38 in patient circuit 34 is any device suitable for communicating an end of conduit 36 with the airway of the patient. Examples of suitable patient interface devices include a nasal mask, oral mask or mouthpiece, nasal/oral mask, nasal cannula, trachea tube, intubation tube, hood or full face mask. It is to be understood that this list of suitable interface devices is not intended to be exclusive or exhaustive.

In the single limb patient circuit of the present invention, exhaled gas from the patient typically exits the patient circuit via an exhaust vent 43, as indicated by arrow D. In the illustrated embodiment, exhaust vent 43 is provided on a distal portion of conduit 34. Depending on the tidal volume of the patient and the pressure delivered by pressure support system 30, a small percentage of the exhaled gas may travel back up the conduit into pressure support system 30 and may even be exhausted to atmosphere through the gas inlet of the pressure generator and/or through a pressure control valve 42, if such a valve is being used with the pressure generator.

Typically, exhaust vent 43 is an orifice provided in the conduit that communicates the interior of the conduit with atmosphere, with no active control over the flow of gas from the system. It is to be understood, however, that a wide variety of exhaust devices and configurations are contemplated for use with the pressure generating system of the present invention. For example, U.S. Pat. No. 5,685,296 to Zdrojkowski et al. discloses an exhalation device and method where the exhalation flow rate through the device remains substantially constant over a range of pressures in the patient circuit. This exhalation device, which is commonly referred to as a plateau exhalation valve or PEV, is suitable for use with the pressure support system of the present invention.

As shown in FIG. 1, pressure support system 30 includes a monitoring system, generally indicated at 44, to monitor the flow and pressure of gas delivered to the patient. In the illustrated embodiment, monitoring system 44 includes a flow sensor 46 that measures a rate at which the breathing gas flows within patient circuit 34. The present invention contemplates that any suitable sensor, such as a conventional pneumatach, can be used for flow sensor 46. It is to be further understood that flow sensor 46 need not be coupled directly to conduit 36. On the contrary, the present invention contemplates the use of any sensor or a plurality of sensors that can quantitatively measure airflow in the patient circuit. For example, flow in the system can be measured at the patient interface device or can be measured or estimated from the motor or piston speed or from torque used to provide the elevated pressure by pressure generator 40. In short, the present invention contemplates any conventional technique for measuring the flow of gas delivered to the patient.

Monitoring system 44 also includes a pressure sensor 48 that detects the pressure of the gas at the patient. In the illustrated embodiment, pressure sensor 48 is in fluid communication with patient interface device 38 via a conduit 36. In this embodiment, the pressure at the patient is estimated based on the known pressure drop that occurs in tubing 36. It is to be understood, however, that the patient pressure can be measured directly at patient interface device 38.

Pressure support system 30 includes a controller 50, which is preferably a microprocessor capable of implementing a stored algorithm, that receives the monitored variables, typically from flow sensor 46 and pressure sensor 48, and controls pressure generating system 32 based on these signals. Of course, controller 50 includes the necessary memory and processing capability to implement the features of the present invention. In a preferred embodiment of the present invention, controller 50 is an AMTEL AT91M55800 microcontroller that runs stored software written in C programming language.

The present invention further contemplates that pressure support system 30 includes an input/output interface 52 for communicating, information, data and/or instructions and any other communicatable items, collectively referred to as "data", between a user and controller 50. Examples of common input/output interfaces suitable for this purpose include a keypad and display. Other communication techniques, either hard-wired or wireless, are also contemplated by the present invention. For example, the present invention contemplates providing a smart card terminal that enables data to be loaded into controller 50 from the smart card or loaded onto the smart card from the controller. Other exemplary, interface devices and techniques adapted for use with the pressure support system include, but are not limited to, an RS-232 port, CD reader/writer, DVD reader/writer, RF link, and modem (telephone, cable or other). In short, any conventional technique for providing, receiving, or exchanging data with controller 50 are contemplated by the present invention as input/output device 52.

Controller 50 also performs conventional leak estimation and respiratory cycle monitoring techniques. The present invention contemplates using any conventional technique for calculating leak $Q_{leak}$, which is the leakage of gas from the pressure support system and includes intentional leaks from the exhaust vent and unintentional leaks from the mask-patient interface, for example. The present invention also contemplates using any conventional technique for taking leak into consideration when determining the patient flow $Q_{patient}$, which is the flow of gas at the airway of the patient, and total flow $Q_{total}$, which is the flow of gas typically measured by flow sensor 46. For example, U.S. Pat. No. 5,148,802 to Sanders et al., U.S. Pat. No. 5,313,937 to Zdrojkowski et al., U.S. Pat. No. 5,433,193 to Sanders et al., U.S. Pat. No. 5,632,269 to Zdrojkowski et al., U.S. Pat. No. 5,803,065 to Zdrojkowski et al., U.S. Pat. No. 6,029,664 to Zdrojkowski et al., and U.S. Pat. No. 6,360,741 to Truschel, and pending U.S. patent applications Ser. No. 09/586,054 to Frank et al. and U.S. patent application Ser. No. 09/970,383, to Jafari et al., the contents of each of which are incorporated by reference into the present invention, all teach techniques for detecting and estimating leak and managing the delivery of breathing gas to the patient in the presence of leaks.

The present invention also contemplates using any conventional technique for detecting the inspiratory and expiratory phases of the patient's respiratory cycle. For example, U.S. Pat. No. 5,148,802 to Sanders et al., U.S. Pat. No. 5,313,937 to Zdrojkowski et al., U.S. Pat. No. 5,433,193 to Sanders et al., U.S. Pat. No. 5,632,269 to Zdrojkowski et al., U.S. Pat. No. 5,803,065 to Zdrojkowski et al., U.S. Pat. No. 6,029,664 to Zdrojkowski et al., and pending U.S. patent application Ser. No. 09/970,383 to Jafari et al., all teach techniques for differentiating between the inspiratory and expiratory phases of a respiratory cycle.

B. Prioritized Controllers

The auto-titration technique implemented by pressure support system 30 according to the principles of the present invention is based on controller 50 being programmed to operate in a such a manner that it effectively functions as a set of prioritized controllers 100, with each controller, or control layer in the controller hierarchy, competing for control of the pressure support system, i.e., for control over the pressure delivered to the patient by the pressure generating system.

Figure 2:
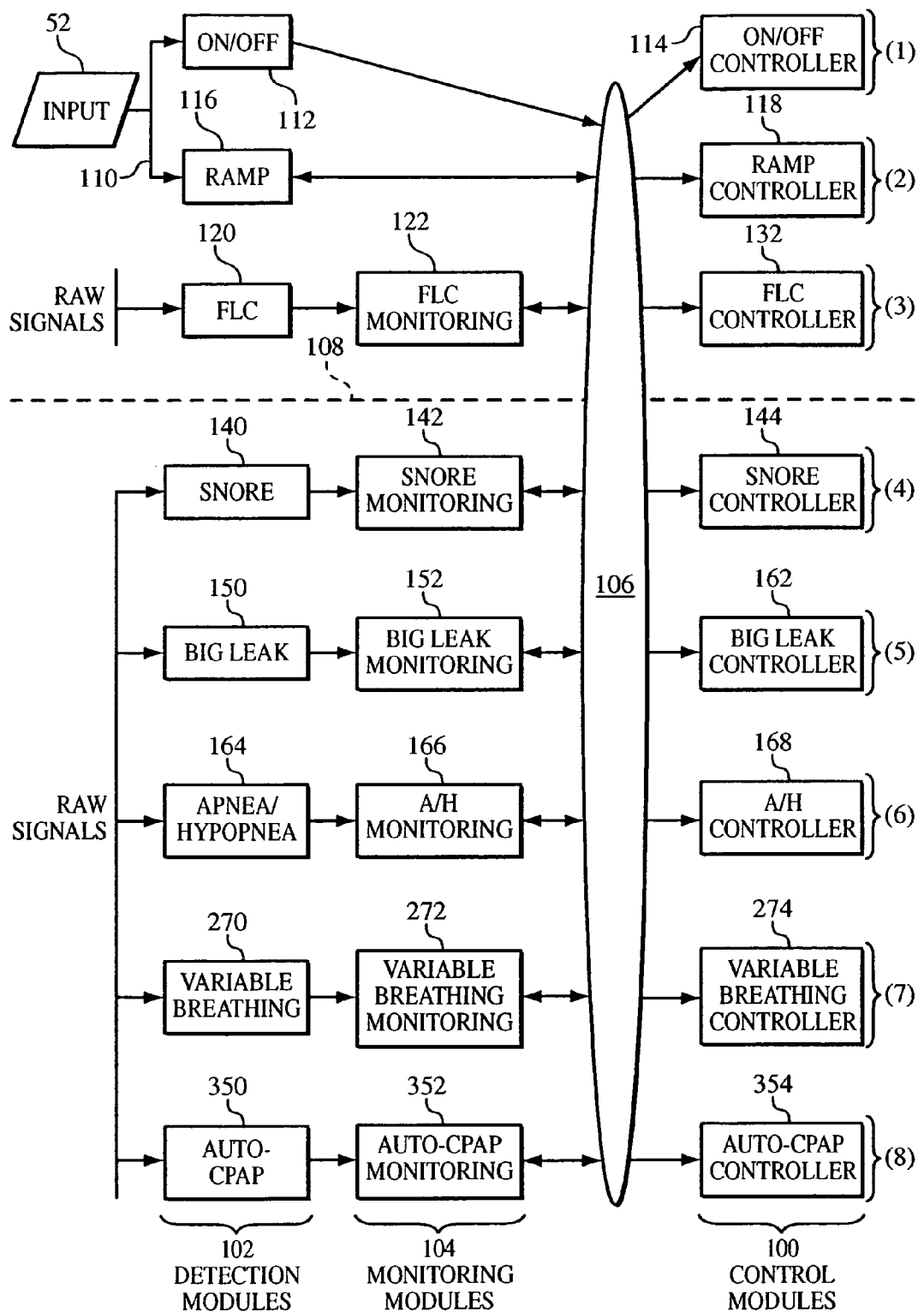
FIG. 2 is a schematic diagram of a control system for implementing the auto-titration technique of the present invention.

FIG. 2 schematically illustrates this prioritized control system, with the priority of each control layer being identified by numerals (1)–(8) on the right side of the figure. The control layer at the uppermost portion of the figure, i.e., having the first (1) priority, is the highest priority controller and takes precedence over all other controllers. The control layer at the lowermost portion of the figure, i.e., having an eighth (8) priority, is the lowest priority controller that only operates if no other controller is operating.

Controller 50 is further programmed to effectively provide a set of detectors or detection modules 102 and a set of monitors or monitoring modules 104 so that an individual detection module and, if necessary, an individual monitoring module is associated with each control layer. Detection modules 102 receive the raw inputs, such as the signal from pressure sensor 48, flow sensor 46, or both. Detection modules 102 also perform any necessary signal processing that may be necessary to provide an input to the associated monitoring module. Monitoring modules 104 determine, from the output of the associated detection module, whether the criteria for requesting activation of an associated control module are satisfied. If so, a request for control of the pressure support system is initiated to a request processor 106, which determines whether control should be turned over to the control module associated with the monitoring module making the request. The algorithm executed by the controller performs the request processing function based on the priority of the control layer that is requesting control of the pressure support system.

Once a controller in a control layer is activated, it controls the operation of the pressure support system and maintains control until the condition that activated the controller is resolved or a higher priority controller takes over. While in control, each controller treats the specific event/condition by performing its control functions, such as adjusting the pressure output from the pressure support system via the pressure generating system. Each controller operates in a unique fashion based on the type of event/condition being treated.

It should be understood that the present invention contemplates setting a prescribed minimum pressure $P_{min}$ and a prescribed maximum pressure $P_{max}$ that serve as absolute pressure boundaries that the pressure support system cannot exceed. Of course, some controllers may have additional constraints on how the pressure is adjusted.

Dashed line 108 in FIG. 2 delineates a difference between control layers that are based on the conditions of the pressure support system and control layers that are based on the monitored condition of the patient. More specifically, control layers having a priority of (1)–(3), which are above line 108, are machine-based control layers that take control of the operation of pressure support system 30 based only on the condition of the pressure support system. On the other hand, control layers having a priority of (4)–(8), which are below dashed line 108, are patient based control layers that take control of the pressure support system based on the monitored condition of the patient.

The control layers can be further subdivided into control layers that operate based on monitored pressure, flow, or both, and control layers that operate based on the manual inputs, such as whether the patient has turned the pressure support system on or activated a pressure ramp. In the presently preferred embodiment of the invention, only the first two controller layers, i.e., the control layers having priority of (1) and (2) are control layers that are based on the manual inputs from the patient or user.

C. First and Second Priority Control Layers

The first priority control layer receives inputs 110 from the input/output device 52. In this first control layer, the input is an indication, typically from an on-/off switch or button, of whether the patient has turned the unit on or off. Naturally, if the patient turns the pressure support off, this should override all other pressure controls, which is why it is given the highest priority in the hierarchy of control layers in the present invention. On/off detection layer 112 determines, from the signal from the on/off switch or other similar device, such as an auto on/off technique noted below, whether the patient has activated or deactivated the pressure support system. Of course, this decision will depend on whether the system is already operating at the time the on/off switch is activated. This indication is provided to request processor 106, where it is deemed to have the highest priority, and all other control operations are overridden so that control of the pressure support system is given over to an on/off controller 114.

On/off controller 114 performs any functions that may be desired or necessary in activating or deactivating the pressure support system. For example, when the pressure support system is deactivated, the pressure support system may perform such processes as storing current pressure settings, compliance information, and other information in a memory or other storage device, in addition to turning off pressure generating system 32. When the pressure support system is activated by the user, the system may perform activation processes, such as reading information from memory or a smart card, retrieving the input settings from the input devices, performing diagnostic functions, resetting lower priority detection, monitoring and control modules, and turning on the pressure generating system.

The second priority control layer also receives inputs 110 from the input/output device 52. In this control layer, the input is an indication, typically from a ramp activation button, of whether the patient has activated a pressure ramp operation. Ramp detection layer 116 determines, from the signal from the on/off switch or other similar device, whether the patient has activated the ramp activation button. If so, this ramp activation request is provided to request processor 106, where it is deemed to have the second highest priority, and all other control operations, other than the on/off control, are overridden, and control is given over to a ramp controller 118.

Ramp control module 118 causes the pressure support system to reduce pressure to a lower setting, such as the system minimum, for a predetermined period of time or for a predetermined number of breathing cycles. The present invention also completes providing a pressure ramp to the patient using any conventional pressure ramping technique, rather than merely dropping the pressure.

In short, when ramp controller 118 assumes control of the pressure support system, it overrides the current pressure delivered to the patient and controls pressure generating system 32 so that relatively low pressure is delivered to the patient. After the elapse of the ramp duration, which can be time based or event based (based on the passage of a predetermined number of breathing cycles) the pressure ramp control is released and another control layer takes over control of the pressure support system. If the ramp feature includes an actual pressure ramp, the pressure is then increased over a period of time, such as 5–35 minutes, or over a predetermined number of breathing cycles. Thereafter, the pressure ramp control is released and another control layer takes over control of the pressure support system. The goal of this embodiment of the present invention is to allow the patient to manually override the pressure provided by the system so that the pressure is reduced to a relatively low level that allows the patient to fall asleep under this relatively low pressure and thereafter, receive the therapeutically beneficial pressure.

If a change in pressure is incorporated into the pressure ramp, the specific shape for the pressure change can be selected by the user, as described, for example, in U.S. Pat. No. 5,682,878 to Ogden, the contents of which are incorporated herein by reference. The duration of the ramp can also be selected by the patient, preprogrammed into the controller, and can depend on whether the ramp activation device has already been activated. For example, U.S. Pat. Nos. 5,492,131; 5,551,418; 5,904,141; 5,823,187; and 5,901,704 all to Estes et al., the contents of which are incorporated herein by reference, describes a pressure ramp technique in which activating the ramp a first time causes the pressure support system to deliver a pressure ramp having a first duration, and a second activation of the ramp causes the system to deliver a pressure ramp having a second duration, which is typically shorter than the first duration. These features can be incorporated in to the operation of ramp controller 118 to determine the shape and duration of each pressure ramp.

D. Flow Limit Control Layer

Figure 3:
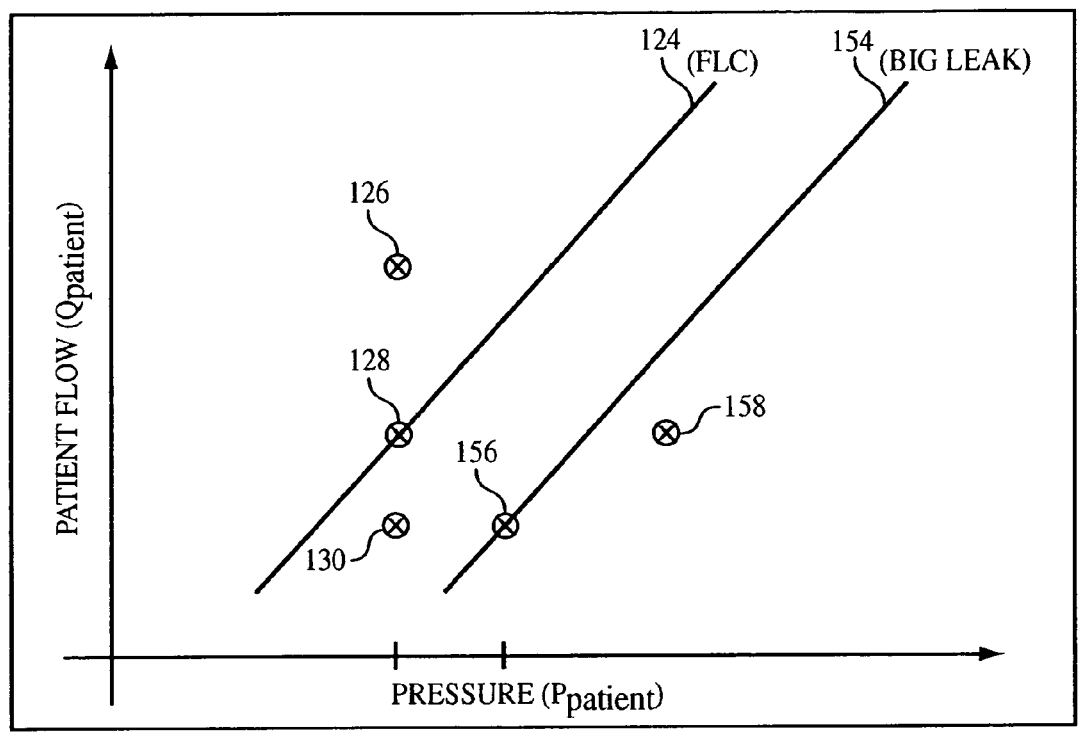
FIG. 3 is a pressure-flow diagram that illustrates the criteria for determining whether to initiate various control features of the auto-titration technique of the present invention.

Flow limit control (FLC) layer, which is assigned a third (3rd) priority, includes an FLC detection module 120 that receives the flow signals from flow sensor 46. FLC detection module 120 compares the total patient flow $Q_{total}$ ($Q_{total}=Q_{patient}+Q_{leak}$) to an empirically developed pressure versus flow curve 124 to determine if a patient disconnect condition, such as a gross system leak or a mask off condition, is occurring. FIG. 3 illustrates a pressure-flow diagram used for this comparison.

As shown in FIG. 3, the operating pressure (horizontal axis) for the pressure support system is either measured via pressure sensor 48 or is known, because the pressure support system knows what pressure it is attempting to deliver to the patient. Pressure-flow curve 124 represents the various flows for each operating pressure level that, if met or exceeded, represent a patient disconnect condition. In other words, FLC detecting module 120 plots the total flow $Q_{total}$, which is directly measured by flow sensor 46 as the flow in patient circuit 34, for the known operating pressure on the chart shown in FIG. 3. If the total flow lies on or above curve 124, as indicated by points 126 and 128, the FLC detector deems a patient disconnect condition to exist. Thus, it is assumed that patient interface device 38 has become disconnected from the patient or some other disconnect condition of the patient circuit has occurred. If, however, the total flow $Q_{total}$ lies below curve 124, as indicated by point 130, FLC detecting module 122 deems there to be no patient disconnect condition.

It can be appreciated that the location of pressure-flow curve 124 in the pressure-flow chart is specific to the hardware used in the pressure support system. For example, a longer patient circuit introduces a greater pressure drop, and, hence, a different pressure flow relationship that would indicate a patient disconnect condition, than that present in a pressure support system with a shorter patient circuit. As noted above, the pressure flow relation 124 is preferably empirically determined for the specific pressure support system. Of course, a number of empirical relationships can be determined in advance, with the specific relationship being selected when the system components are assembled.

Referring again to FIG. 2, if a patient disconnect condition is detected by FLC detector 120, this indication is provided by FLC monitoring module 120, which monitors the duration that the patient flow is above FLC curve 124. If the total flow is at or above FLC curve 124, as indicated by the output of FLC detector 120, for a predetermined period of time, such as 7 seconds, a request for control is sent to request processor 106. The request from FLC monitoring module 122 is assigned the third highest priority, and all other control operations, other than the on/off control 114 and ramp control 118, are overridden, so that control is given over to a FLC controller 132.

The purpose of the seven second time delay is to ensure that deep inhalations by a patient, which may cause the total flow to move outside the FLC curve temporarily, are not erroneously considered as a patient disconnect condition. It can be appreciated that other duration time delays can be used so long as temporary, patient induced flows are not erroneously deemed to be a disconnect condition. The present invention further contemplates that if the FLC condition exists for a relatively long period of time, such as 90 seconds, it is assumed that the patient has removed the patient interface device. In which case, the system will automatically turn itself off via well known auto on/off techniques. See, e.g., U.S. Pat. No. 5,551,418 to Estes, et al., which teaches techniques for automatically turning a pressure support system off or on depending on whether the patient is using the system.

FLC controller 132, once activated, causes the pressure delivered to the patient to be lowered to a low level that allows the user to correct the disconnect condition without having to fight the pressure/flow that would otherwise be delivered by the pressure support system. This lower pressure level delivered by FLC controller 132 should be low enough to allow the patient to reapply the mask without discomfort, yet high enough to allow the pressure support system to detect when the patient has reapplied the mask.

FLC controller 132 also causes the pressure generating system to continue to deliver the flow of breathing as at this lower level until the disconnect condition is corrected, i.e., until the measured total flow $Q_{total}$ falls below curve 124 so that control is no longer requested by FLC monitoring module 122, or until a time period that initiates the auto-off function elapses. In a preferred embodiment of the present invention, when the patient disconnect condition is corrected, FLC controller 132 ramps the pressure delivered to the patient back up to a prior pressure level to provide normal flow.

E. Snore Control Layer

Snore control layer, which is assigned a fourth (4th) priority, includes a snore detection module 140 that receives inputs from monitoring system 44, such as pressure sensor 48 and/or flow sensor 46, and determines from this information whether the patient is experiencing a snore. The present invention contemplates that the decision as to whether the patient is experiencing a snore can be made using any conventional snore detection technique, such as those described in U.S. Pat. Nos. 5,203,343; 5,458,137; and 6,085,747 all to Axe et al. However, in a preferred embodiment of the present invention, the determination of whether the patient is experiencing a snore is made according to the teachings of U.S. provisional patent application, entitled "Snore Detecting Method and Apparatus" to Truschel et al. and filed on Oct. 10, 2001, the contents of which are incorporated herein by reference.

The present invention also contemplates further discriminating the snore event based on whether the snore event occurs in the inspiratory or the expiratory phase of a respiratory cycle. During either phase of the respiratory cycle, the threshold above which a snore event would nominally be declared can be dependent upon some additional parameter(s), such as that measured by pressure sensor 48 in FIG. 1. For higher pressures, the snore detection threshold could be raised, thus making it more difficult to detect a snore event. The value of the snore detection threshold could be independently settable for each respiratory phase. This implies that for a specific parameter, such as pressure, the threshold at which a snore event would be declared for the inspiratory phase could be either higher, lower, or the same as the threshold setting for the expiratory phase. It is to be understood that other parameters, in addition to pressure, or a combination of parameters, could be used to set the threshold at which a snore event is declared.

Snore detection module 140 provides an output to snore monitoring module 142 each time a snore event is declared. Snore monitoring module 142 determines, based on the detected snore events, whether to initiate a request for control of the pressure support system from request processor 106. According to a presently preferred embodiment, snore monitoring module 142 includes a counter that counts the number of snore events and a timer to measure the length of time between snore events. If a snore event does not occur within 30 seconds of the last snore event, then the counter is reset to zero. If the counter reaches three, a request for control is sent to request processor 106. Thus, if three snore events occur, where each snore event is not longer than 30 seconds from the last snore event, a request for control is initiated. This request expires after 30 seconds and the snore counter in snore monitoring module 142 is reset.

The request from snore monitoring module 142 is assigned the fourth highest priority, and all other control operations, other than the on/off control 114, ramp control 118, and the FLC control 132, are overridden, so that control is given over to a snore controller 144. If the request process results in control being given to snore controller 144, the snore controller causes pressure generating system 32 to raise the pressure delivered to the patient by 1.0 cmH$_2$O. In a preferred embodiment, this pressure increase is done at a rate of 1 cmH$_2$O per 15 seconds.

Snore controller 144 releases control, and as a background task, sets up a one minute lockout interval. The pressure at the end of the pressure increase is stored as a snore treatment pressure. It is believed that this snore treatment pressure represents a pressure level that provides a relatively good treatment to the patient to treat many of the breathing disorders he or she may experience.

The lockout interval also prevents the pressure support system from attempting to over-treat the patient with another pressure increase if, for example, additional snore events occur that would otherwise cause the snore controller to increase pressure. If, however, additional snore events occur that meet the above-described criteria required by snore monitoring module 142 and the lockout interval has elapsed, the snore monitoring module will again request control and, if granted, snore controller 144 will again increase pressure (up to the maximum pressure set point). This new pressure is stored as the snore treatment pressure.

It is to be understood that the number of snore events used in snore monitoring module 142 to determine when to request control of the pressure support system, the amount and rate of the pressure increase provided by snore controller 144, and the duration of the lockout can be varied.

F. Big Leak Control Layer

The big leak control layer, which is assigned a fifth (5th) priority, is somewhat similar to the FLC control layer in that this control layer analyzes the estimated patient circuit leak Q$_{leak}$ and compares it to another empirically developed pressure versus flow curve. However, this control layer is not attempting to determine whether the patient has removed the patient interface device or whether a patient circuit disconnection or other gross leak event has occurred. Rather, the big leak control layer attempts to determine when the estimated leak from the system exceeds a reliable range of operation.

Big leak control layer, includes a big leak detection module 150 that receives the flow signals from flow sensor 46. Big leak detection module 150 determines, the estimated leak Q$_{leak}$ from this signal using any conventional leak estimation technique and sends this information to big leak monitoring module 152. In big leak monitoring module 152, the estimated leak is compared to an empirically developed curve to determine if the leak from the system exceeds a worse case leak.

Referring again to FIG. 3, the operating pressure (horizontal axis) for the pressure support system is known. Curve 154 represents the various flows for each operating pressure levels that, if exceeded, represent a leak that is larger than the worst case system leak. In other words, big leak monitoring module 152 plots the estimated leak Q$_{leak}$ for the known operating pressure on the chart shown in FIG. 3. If the estimated leak is above curve 154, as indicated by points 126, 128, and 130, the estimated leak exceeds the leakage flow that constitutes a reliable operating range for the pressure support system. This can occur, for example, if the patient interface device becomes partially dislodged from the patient so that more gas is leaking from the patient circuit than would otherwise be expected for the type of patient circuit being used. If, however, the estimated leak Q$_{leak}$ lies on or below curve 154, as indicated by points 156 and 158, big leak monitor 152 deems there to be an acceptable level of system leak.

It can be appreciated that the specific location of curve 154 in the pressure-flow chart is specific to the hardware used in the pressure support system. For example, different size exhaust devices that allow different exhaust flows would require different pressure-flow relationships. Pressure-flow relation 154 is preferably empirically determined for the specific pressure support system. Of course, a number of empirical relationships can be determined in advance, with the specific relationship being selected when the system components are assembled.

Referring again to FIG. 2, if a big leak condition is detected by big leak monitoring module 152, a request for control is sent to request processor 106. As noted above, the request from big leak monitoring module 152 is assigned the fifth highest priority, and all other control operations, other than on/off control 114, ramp control 118, FLC control 132, and snore control 144, are overridden, so that control is given over to big leak controller 162.

Once control is given to big leak controller 162, this controller causes the pressure delivered to the patient by pressure generating system 32 to be lowered by a predetermined amount, at a predetermined rate, for a predetermined period of time. For example, a presently preferred embodiment of the present invention contemplates reducing the pressure delivered to the patient by 1 cmH$_2$O over a period of 10 seconds and holding at this new pressure for 2 minutes.

Big leak detection module 152 will continue to request that big leak controller assume control of the pressure support system so long as the criteria necessary to satisfy the big leak monitoring module are met. If the request is again granted, after the 2 minute hold, the big leak controller would repeat the pressure reduction and hold process until the big leak condition is resolved or minimum pressure is reached. The big leak condition must also clear for a predetermined period of, such as 90 seconds, before control is released by this control layer.

One potential result of the big leak control layer is that this pressure drop may arouse the patient at least slightly. It is believed that the big leak condition will be resolved if this arousal causes the patient either to roll over and inadvertently reposition the mask or wake up and adjust the mask. It is also believed that by lowering the pressure, the patient interface device may reseat itself, thereby eliminating the big leak condition.

G. Apnea/Hypopnea Control Layer

Apnea/hypopnea (A/H) control layer, which is assigned a sixth (6th) priority, includes an A/H detection module 164 that receives inputs from monitoring system 44, and, in particular flow sensor 48, and determines, from this information, whether the patient is experiencing an apnea or a hypopnea. This determination is provided to A/H monitoring module 166 that decides whether to request that an A/H control module 168 take control of the pressure generating system.

The present invention contemplates that A/H detection module 164 monitors the variation of the inspiratory peak flow, referred to as the weighted peak flow ($Q_{Wpeak}$), and determines from the weighted peak flow, as discussed in detail below, whether the patient is experiencing an apnea or hypopnea. Thus, in order to understand the operation of the A/H control layer, it is necessary to first understand how the present invention determines the weighted peak flow ($Q_{Wpeak}$).

1. Weighted Peak Flow

Figures 4A, 4B, 4C:
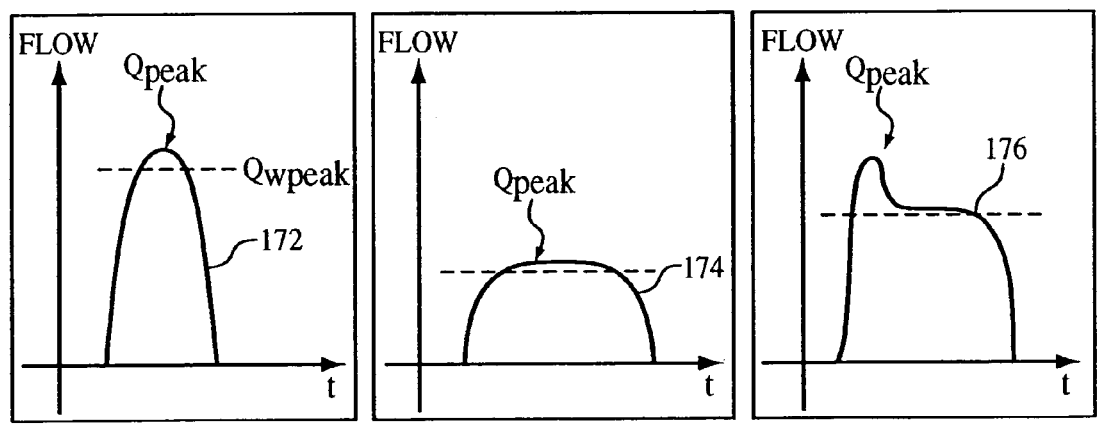
FIGS. 4A–4C illustrate further exemplary waveforms that illustrate the difference between an actual peak flow and a weighted peak flow $Q_{W_{peak}}$ used by the present invention.
Figure 5:
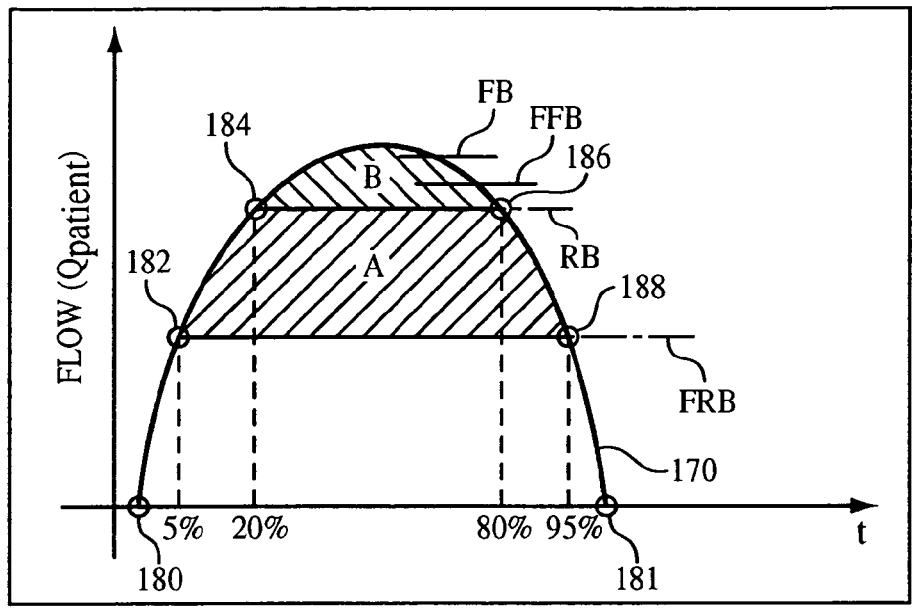
FIG. 5 is a graph illustrating an exemplary inspiratory waveform for explaining how the present invention calculates various parameters used in performing the auto-titration functions.

FIG. 5 is a graph of an exemplary inspiratory waveform 170 of the patient flow, and FIGS. 4A–4C are graphs illustrating the difference between an actual peak flow and a weighted peak flow $Q_{Wpeak}$ used by the present invention. As shown in FIGS. 4A–4C, which illustrate different exemplary inspiratory waveforms 172, 174 and 176, respectively, the actual peak $Q_{peak}$ is the high point on the inspiratory waveform. It can be appreciated from FIGS. 4A–4C that the highest peak flow may be of little clinical value. For example, in FIG. 4C the peak flow is exaggerated due to the flow overshoot at the start of inspiration. For this reason, the present invention does not use $Q_{peak}$. Instead, the present invention uses the weighted peak flow $Q_{Wpeak}$, the approximate location of which is shown by the dashed lines in FIGS. 4A–4C.

Referring now to FIG. 5, to determine $Q_{Wpeak}$ for an inspiratory waveform, such as flow waveform 170, the present invention first determines a start point 180 and a stop point 181 for the inspiratory waveform. This is accomplished using any conventional technique. The total volume of the inspiratory flow is then calculated. Again, this can be accomplished using any conventional technique. Next, the system determines the points on the inspiratory waveform that correspond to the 5% volume (point 182), 20% volume (point 184), 80% volume (point 186), and 95% volume (point 188). The next steps require determining two baseline levels, a Flatness Round Baseline (FRB) and a Roundness Baseline (RB).

The Flatness Round Baseline (FRB) is determined by comparing all of the flow values of the points on the waveform between the 5% and the 95% volume points against the flow values at the 5% and 95% volume points. This is done to find the lowest point from among the range of points between 5% and 95%, which is used to set the FRB. A line drawn at the lowest point from among these points defines the FRB.

The Roundness Baseline (RB) is determined by comparing all of the flow values of the points on the waveform between the 20% and the 80% volume points against the flow values at the 20% and 80% volume points. This is done to find the lowest point from among the range of points between 20% and 80%, which is used to set the RB. A line drawn at the lowest point from among these points defines the RB.

The system also calculates two further baselines; a Flatness Flat Baseline (FFB) and a Flatness Baseline (FB), based on the Flat Roundness Baseline (FRB) and the Roundness Baseline (RB), respectively. More specifically, the FFB is determined as the average of all flow measurements above the FRB and between the 5% and 95% volume points. In most cases, this will correspond to the flow measurements between the 5% and the 95% volume points, as shown in FIG. 5. However, it is possible for the FRB to be below the 5% or 95% volume shown in FIG. 5. It can be appreciated that finding the average of the flow measurements from the start to the end of the FRB line is equivalent to determining the volume of areas A and B in FIG. 5 and dividing this volume by the period of time ($T_{5\%-95\%}$) between the 5% volume and the 95% volume.

The Flatness Baseline (FB) is determined as the average of all flow measurements above the RB and between the 20% and 80% volume points. In most cases, this will correspond to the average of all flow measurements between the 20% and the 80% volume points. However, it is possible for the RB to be below the 20% or 80% volume shown in FIG. 5. It can be appreciated that finding the average of the flow measurements from the start to the end of the RB line is equivalent to determining the volume of area B in FIG. 5 and dividing this volume by the period of time ($T_{20\%-80\%}$) between the 20% volume and the 80% volume. The Flatness Baseline level is the weighted peak flow $Q_{Wpeak}$.

2. Apnea/Hypopnea Detection Criteria Modeling

Figure 6:
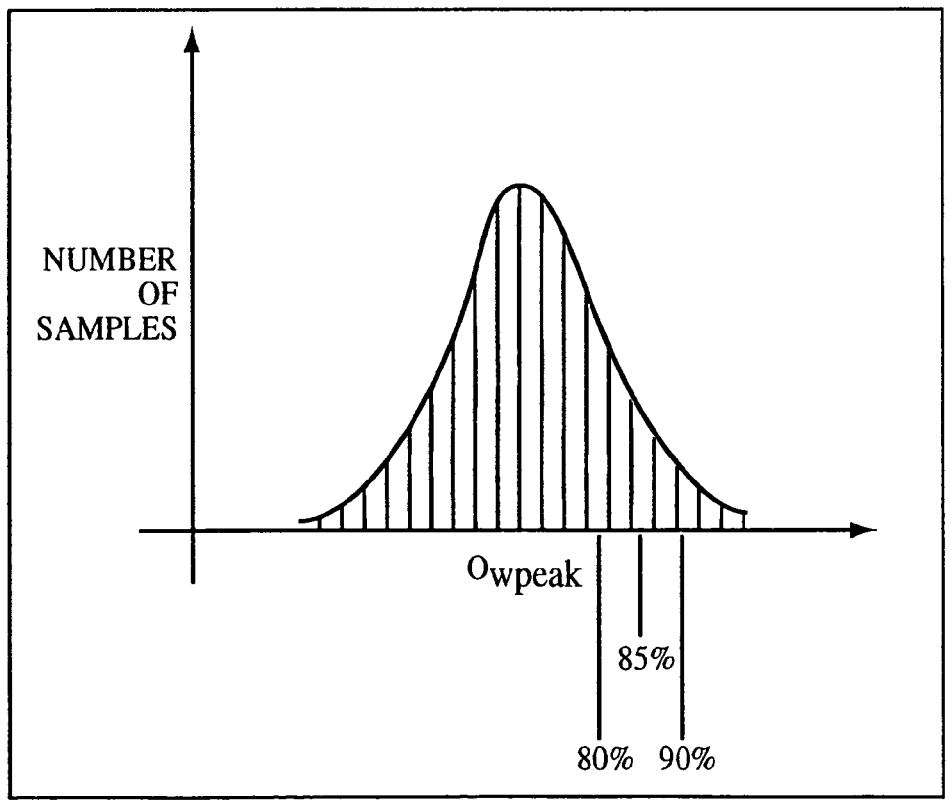
FIG. 6 is an exemplary histogram of the weighted peak flows for the breaths accumulated during the moving window time period.
Figure 7A:
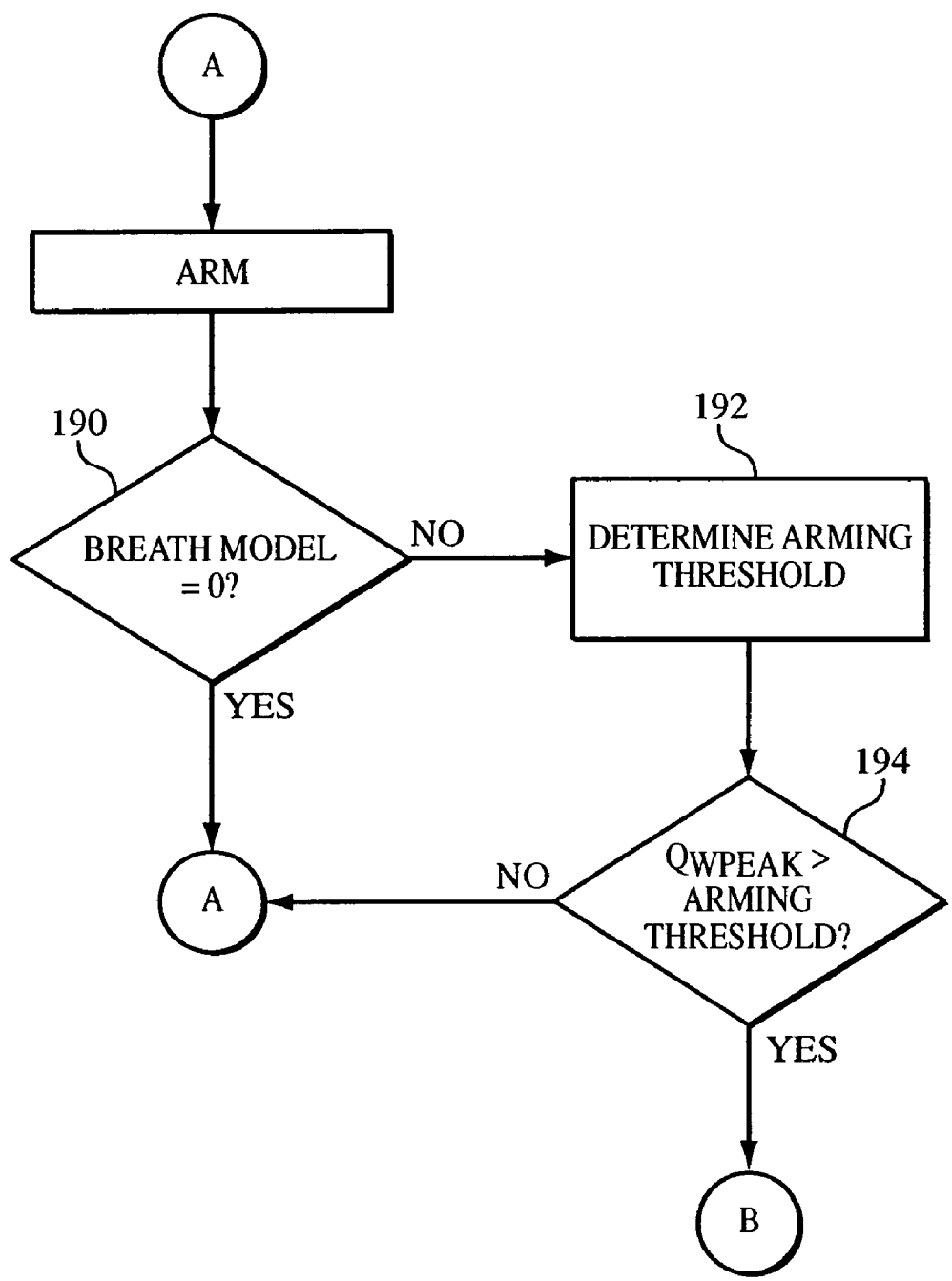
FIGS. 7A–7E are flow charts illustrating the hypopnea detection process according to the principles of the present invention.
Figure 7C:
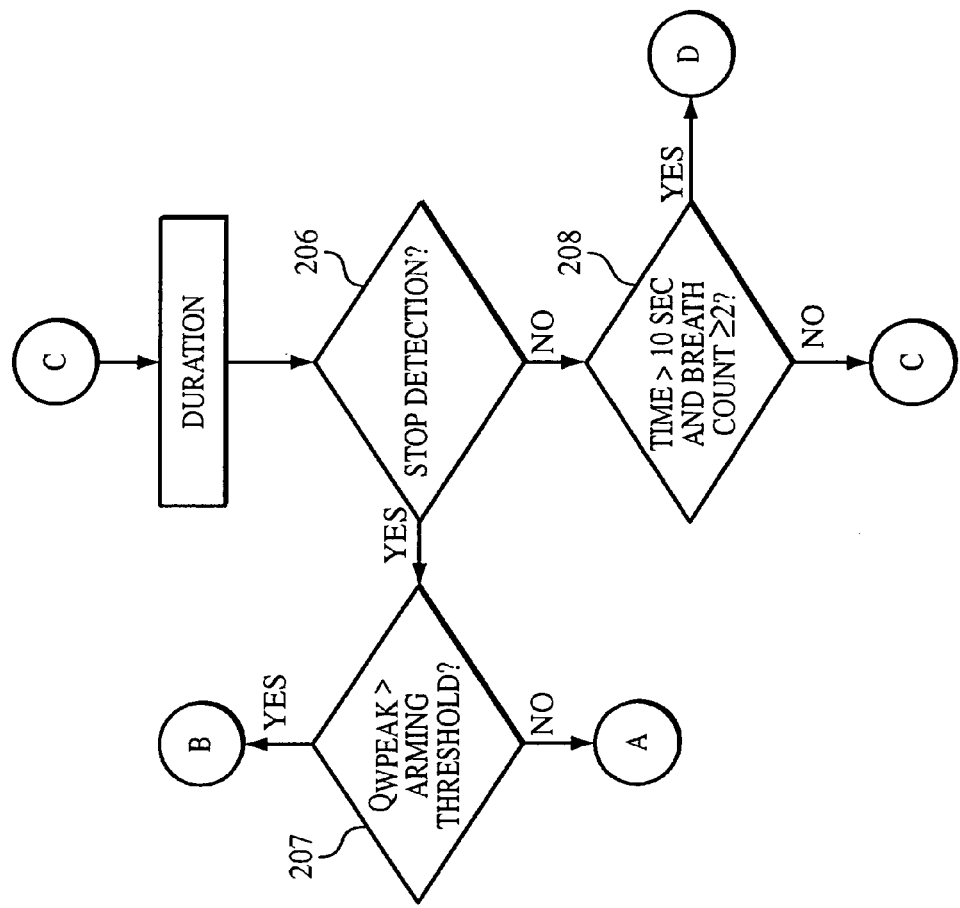
Figure 7B:
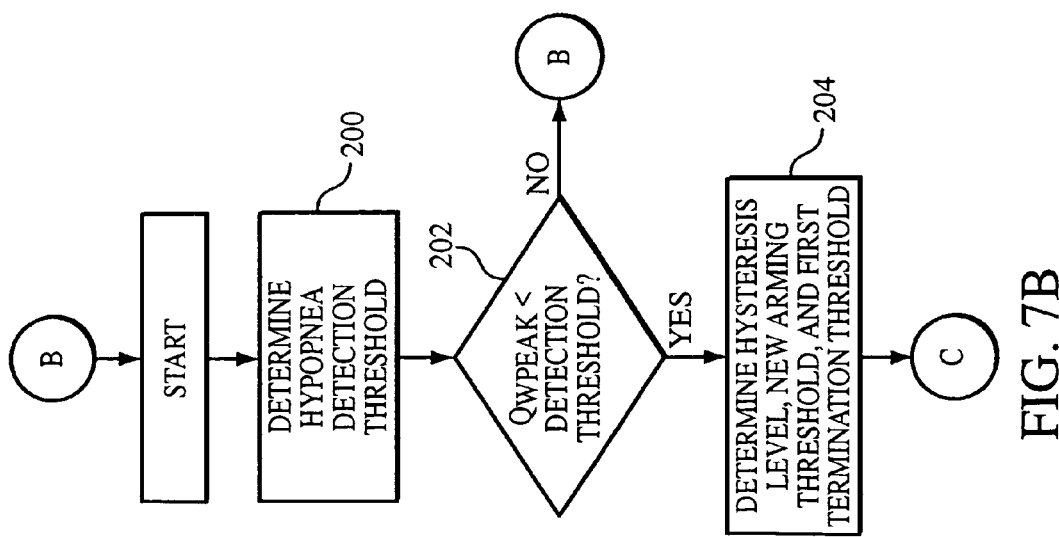
Figure 7E:
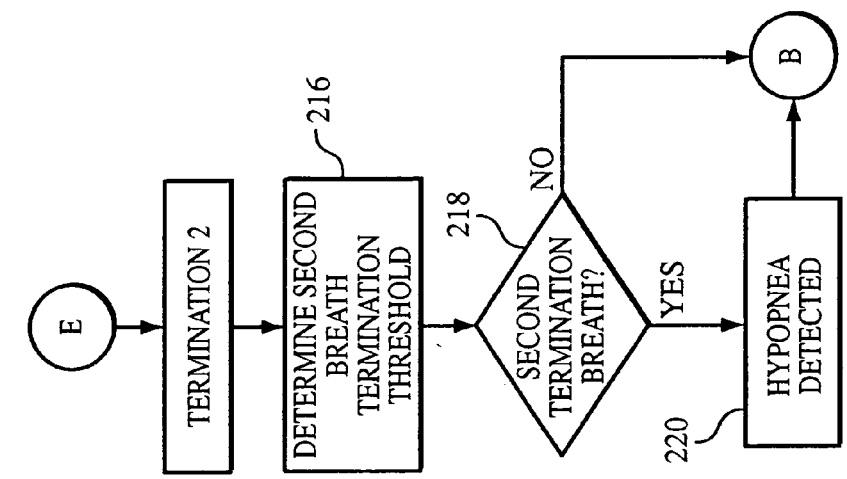
Figure 7D:
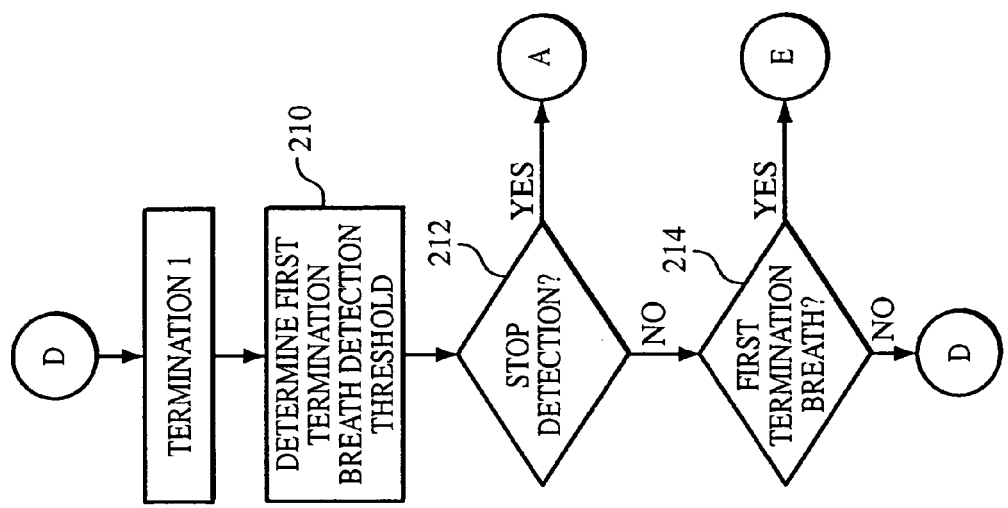

Apnea/hypopnea detection module 164 gathers weighted peak flow $Q_{Wpeak}$ information over a period of time to determine a model weighted peak flow $Q_{WPM}$, which is used for comparison purposes in performing the hypopnea and apnea detection processes discussed below. In particular, A/H detector 164 monitors the weighted peak flows for the inspiratory breaths occurring over a 4 minute moving window. These weighted peak flows are statistically sorted as shown in FIG. 6, which is an exemplary histogram of the weighted peak flows for the breaths accumulated during the moving window.

In one embodiment of the present invention, the model peak weighted peak flow $Q_{WPM}$ is determined as the weighted peak flows falling at the 85th percentile of the accumulated weighted peak flows. However, in a preferred embodiment of the present invention, the weighted peak flows falling between the 80th and 90th percentiles are averaged, and this average value is taken as the model peak weighted peak flow $Q_{WPM}$.

3. Hypopnea Detection

FIGS. 7A–7E are flow charts illustrating the hypopnea detection process carried out by A/H detector 164 according to the principles of the present invention. The hypopnea detection begins in step 190 where a determination is made as to whether the model weighted peak flow $Q_{WPM}$ exists. The model weighted peak flow $Q_{WPM}$ can be reset, for example, if a high leak level or rapid changes in the leak level are detected. In which case, there would not be enough information from which to determine whether the patient is experiencing a hypopnea. Therefore, if there is not enough data to generate the model weighted peak flow $Q_{WPM}$, the system continues to collect data to generate this information. If the model weighted peak flow $Q_{WPM}$ exists, the system moves to step 192.

In step 192, an arming threshold is determined. The purpose of the arming threshold is to ensure that the patient has at least one relatively large breath going into the hypopnea. This relatively large breath should have a weighted peak that is outside the hypopnea detection range, so that smaller breaths that are within this range can be detected. Without first finding a breath that is outside the hypopnea detection range, it would difficult, for example, to determine whether the patient has started a new hypopnea or is merely continuing an existing hypopnea. In an exemplary embodiment of the present invention, the arming threshold is set to 60% of the current model weighted peak flow $Q_{WPM}$.

In step 194, the current weighted peak flow $Q_{Wpeak}$ is compared to the arming threshold to look for the relatively large entry breath. If no such breath is detected, i.e., if the current weighted peak flow $Q_{Wpeak}$ is less than the arming threshold, the system returns to step 190 and this process repeats. If, however, a breath having a weighted peak flow $Q_{Wpeak}$ that is outside the arming threshold is detected, the system moves to step 200.

In step 200, the hypopnea detection threshold is determined as 50% of the model weighted peak flow $Q_{WPM}$. In step 202 a weighted peak flow $Q_{Wpeak}$ for a current inspiratory phase is compared to the detection threshold calculated in step 200. If the current weighted peak flow $Q_{Wpeak}$ is greater than or equal to 50% of the model weighted peak flow $Q_{WPM}$, the system returns to step 200. If, however, the current weighted peak flow $Q_{Wpeak}$ is less than 50% of the model weighted peak flow $Q_{WPM}$, the system moves to step 204 and begins monitoring for the occurrence of a hypopnea event.

In step 204, the model weighted peak flow $Q_{WPM}$ at the start of the hypopnea detecting is clamped or latched for use in determining other thresholds. This clamped value $Q_{WPM}$ clamped for the model weighted peak flow $Q_{WPM}$ is used to determine a hysteresis level. The hysteresis level is set to 60% of $Q_{WPMclamped}$ and the system moves to step 206. The clamped value $Q_{WPMclamped}$ is also used to set a first termination threshold, which is the weighted peak flow $Q_{Wpeak}$ that must be met by a monitored inspiratory waveform in order to terminate the hypopnea detection process. The first hypopnea termination threshold is set at 75% of $Q_{WPMclamped}$. In step 204 a new arming threshold is calculated. This is done because the arming threshold calculated in step 192 may no longer be valid, especially if a significant amount of time has passed since the arming threshold was calculated in step 192. The arming threshold is set to 60% of the current model weighted peak flow $Q_{WPM}$.

In step 206 a decision is made whether to stop the hypopnea monitoring process. This may occur, for example, if a discard event occurs or if the weighted peak flow exceeds the hysteresis level. A discard event occurs, for example, when the data provided to the detection module includes an aberration or is incomplete. If the hypopnea monitoring process stops in step 206, the system, in step 207, checks the current weighted peak flow $Q_{Wpeak}$ against the arming threshold, which is the arming threshold calculated in step 204. If the current weighted peak flow $Q_{Wpeak}$ is greater than the arming threshold, the system returns to step 200. If the current weighted peak flow $Q_{Wpeak}$ is less than or equal to the arming threshold, the system returns to step 190.

The reason for returning to step 200, rather than step 190 if the current weighted peak flow $Q_{Wpeak}$ is greater than the arming threshold, is because the patient is already having breaths that are large enough to determine that a hypopnea is occurring. Thus, there is no need to recalculate the arming threshold, so instead, the system returns to step 200 to begin looking for a hypopnea.

If the hypopnea monitoring process continues from step 206, the system determines in step 208 whether a sufficient amount of time has elapsed with the weighted peak flow $Q_{Wpeak}$ being below the hypopnea detection threshold and whether a sufficient number of breathing cycles have occurred. In the presently preferred exemplary embodiment, the weighted peak flow must be below the hysteresis threshold for at least 10 seconds and there must be at least two detectable breathing cycles in order to be confident that the patient is experiencing a hypopnea. Thus, in step 208, a determination is made whether 10 seconds have elapsed and whether two breathing cycles having non-zero peak flow levels have occurred. If not, the system returns to step 206. If so, the system begins monitoring for a first termination breath in step 210. The first termination breath is a breath that ends the hypopnea event.

During the hypopnea event, i.e., once the hypopnea monitoring began in step 204, the minimum weighted peak flows were being monitored. In step 210, the two lowest minimum weighted peak flows that have been detected so far are averaged. This average value is then doubled and used as a second hypopnea termination criteria in monitoring for the first termination breath. The purpose of this second hypopnea termination criteria is to allow large deviations from the relatively low peak levels that occur during a hypopnea to terminate the hypopnea monitoring process. Please also recall that the first hypopnea termination criteria was determined in step 204 as 75% of $Q_{WPMclamped}$.

In step 212, a decision is made whether to stop the hypopnea detection process. This will occur if, for example, a discard event occurs or if the hypopnea has lasted beyond a duration normally associated with a true hypopnea event. In the presently preferred embodiment, this duration is 60 seconds. Thus, in step 212, the system determines whether the hypopnea conditions have been met for more than 60 seconds. If so, the hypopnea detection process is stopped, all logic flags are reset, and the process returns to step 190. If the hypopnea detection process continues, a determination is made in step 214 whether the weighted peak flow for the current breath meets the first or second termination threshold.

If the weighted peak flow for the current breath is greater than 75% of $Q_{WPMclamped}$ (first hypopnea termination criteria) or if the weighted peak flow for the current breath is greater than two times the average of the two, non-zero, lowest weighted peak flows (second hypopnea termination criteria), a valid first termination breath is declared, and the system processes to step 216. If a valid first termination breath is not detected in step 214, the system returns to step 210 and continues to monitor for a first termination breath.

Once a first termination breath is detected in step 214, the next proceeding breath must meet a third hypopnea termination threshold, which is determined in step 216. The third hypopnea termination threshold is set, in step 214, at 80% of the minimum of the first and second termination criteria thresholds.

In step 218, it is determined whether the weighted peak flow of next breath immediately after the first termination breath is 80% of the minimum of the first and second termination criteria thresholds. If so, the hypopnea monitoring process is terminated and a hypopnea is declared detected in step 220. If not, the hypopnea detection process is stopped, all logic flags are reset, and the process returns to step 200.

In summary, in order to detect a hypopnea, the following criteria must be met:

a) Valid model weighed peak flow data $Q_{WPM}$ must exist (step 190);
b) There must be an entry breath that is outside the hypopnea detection range (steps 192 and 194);
c) The weighted peak flow of a breath must fall below the hypopnea detection threshold (step 202);
d) The weighted peak flow of subsequent breaths must remain below the hysteresis threshold for at least 10 seconds and at least two breaths must be detected (steps 206 and 208);
e) The weighted peak flow of a breath must rise above the lesser of the first termination threshold or the second termination threshold (step 214) and the next breath must be above a third termination threshold which set based on the first and second termination thresholds;

f) The duration of the hypopnea event must not exceed 60 seconds (step 212); and g) A discard event must not occur (steps 206 and 212).

4. Apnea Detection

As with hypopnea detection, A/H detection module 164 determines whether the patient is experiencing an apnea by comparing the weighted peak flow $Q_{Wpeak}$ for each breathing cycle to the model weighted peak flow $Q_{WPM}$. More specifically, an apnea detection process starts if the current weighted peak flow $Q_{Wpeak}$ falls below 20% of the model weighted peak flow $Q_{WPM}$. When this occurs, the model weighted peak flow $Q_{WPM}$ at the start of the apnea monitoring process is clamped or latched. This clamped value $Q_{WPMclamped}$ is also used to set an apnea termination threshold, which represents the weighted peak flow that must be met by a monitored inspiratory waveform in order to terminate the apnea detection process. The apnea termination threshold is set as 30% of $Q_{WPMclamped}$. In this case, the apnea takes precedence and overrides, resets, or temporarily disables the hypopnea detection.

Once an apnea monitoring process begins, if the weighted peak flow remains below the termination threshold for a predetermined period of time, which in a preferred embodiment is 10 seconds, a start of apnea event is declared. It should be noted that both the hypopnea and apnea detection take place concurrently.

Figure 8:
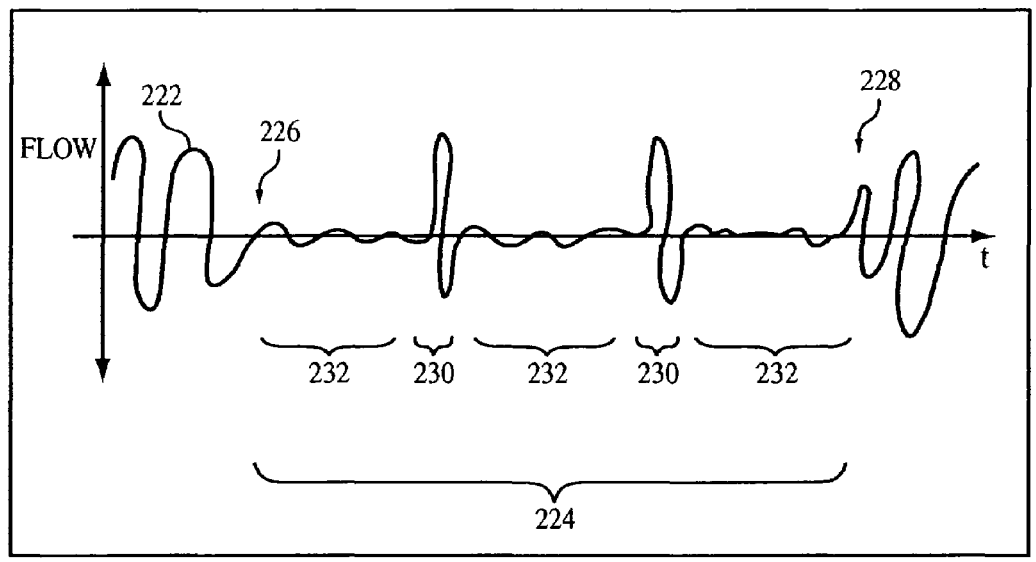
FIG. 8 is an exemplary embodiment of a patient flow waveform for use in describing the gap filling process used in the apnea detection technique of the present invention.

The present inventors appreciated that during an apnea event, the patient may sometimes make a momentary respiratory effort. FIG. 8 illustrates an exemplary patient flow waveform 222 in which an apnea 224 begins generally at 226 and terminates generally at 228. During apnea 224, the patient made a respiratory effort having very short duration, yet relatively high peak flow, identified as respiratory bursts 230. During periods 232, before and after these bursts, the patient flow was at a relatively low level typical of an apnea. The present invention contemplates effectively ignoring transient bursts 230 in monitoring for the occurrence of an apnea. If these bursts are not ignored, there is a chance that an apnea detector could erroneously consider the burst, and, thus, disregard this sequence as an apnea.

5. Apnea/Hypopnea Monitoring

The occurrence of a hypopnea event and the start of an apnea event are reported by A/H detector 164 to A/H monitor 166, which then must determine whether to request that A/H controller 168 take control of the pressure generating system. In a presently preferred embodiment of the invention, A/H monitor 166 will issue a request for control to request processor 106 if two apnea events or if two hypopnea events, as determined in the manner discussed above by A/H detector 164, occur within a predetermined period of time. In a presently preferred embodiment, this period of time is a three minute moving window. However, those skilled in the art can appreciate that the period for this window can be varied.

The present invention also contemplates causing A/H monitor 166 to issue a request for control to request processor 106 if a mixture of apnea events and hypopnea events occur. For example, if two apnea or hypopnea events occur within a predetermined period of time, A/H monitor would issue the control request.

6. Apnea/Hypopnea Pressure Control

Once A/H controller 168 is granted control, it initially gradually raises pressure 1 cmH$_2$O and holds the pressure at this level for 30 seconds. After the 30 second hold period, the controller then releases control (usually to an auto-CPAP controller hold state discussed below). If the criteria for granting control to A/H controller 168 are met again, the controller repeats this process and raises the patient pressure 1 cmH$_2$O and executes the 30 second hold. A/H controller 168 can increase pressure to 8 cmH$_2$O without restriction. If apneas or hypopneas are detected at pressures greater than 8 cmH$_2$O, an additional pressure control restriction is invoked as described below.

In the embodiment of the present invention described thus far, A/H detection module 164 cannot detect the difference between obstructive apnea/hypopnea events and central apnea/hypopnea events, but compensates for this using A/H controller 168. More specifically, the A/H controller is limited or in some cases restricted from increasing the pressure if the pressure is already above a threshold. Obstructive events can be resolved by increasing pressure. However, it is generally believed that central apneas are not responsive to pressure increases. Therefore, if the pressure was increased as a result of the occurrence of an apnea, and further apneas occur, it is assumed that the apneas that are occurring at the relatively high pressure, e.g., 11 cmH$_2$O, are central, and not obstructive, apneas. In which case, additional pressure increases are not desired.

To achieve this goal, A/H controller 168 sets a target apnea/hypopnea treatment limit when an apnea or hypopnea control request is made by A/H monitoring module 164. In a presently preferred embodiment, the target apnea/hypopnea treatment limit is set at 3 cmH$_2$O above the pressure being delivered to the patient when A/H monitor 164 initiated a control request. If, however, the patient pressure is 8 cmH$_2$O or less, the target apnea/hypopnea treatment limit is set at 11 cmH$_2$O. Once set, the target apnea/hypopnea treatment limit remains in place until a period of time elapses where there are no new apnea/hypopnea events. The present invention currently contemplates setting this interval to 8 minutes, so that if 8 minutes go by after the target apnea/hypopnea treatment limit was set without any new apnea/hypopnea control requests, the target apnea/hypopnea treatment limit is cleared.

Figure 9:
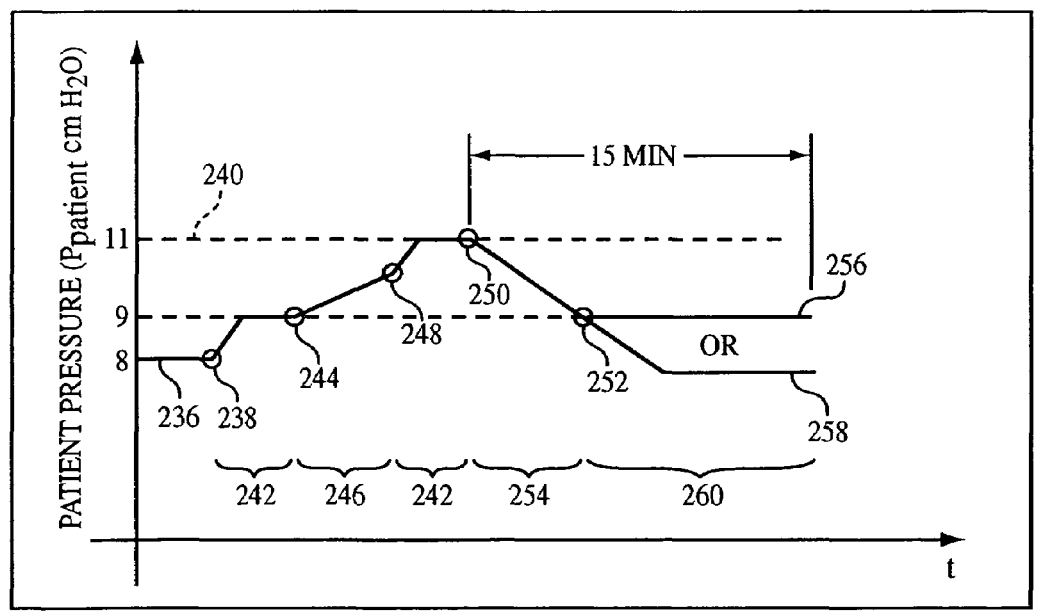
FIG. 9 illustrates an exemplary patient pressure to describe the operation of the apnea/hypopnea treatment procedure of the pressure support system.

Referring now to FIG. 9, which illustrates an example pressure curve 236 for the patient pressure generated by the pressure support system, if an apnea/hypopnea control request is granted at point 238, where the patient is currently at 8 cmH$_2$O, the target apnea/hypopnea treatment limit 240 is set at 11 cmH$_2$O. A 1 cmH$_2$O pressure increase and 30 second hold are then performed during an A/H treatment interval 242, and control is released by A/H controller 168 at point 244. During interval 246 control of the pressure support system is being handled by some other control module, such as the auto-CPAP module discussed below. For purposes of this example, the patient pressure was increased during this interval by 1 cmH$_2$O. At point 248, which is at 10 cmH$_2$O, another apnea/hypopnea control request is granted, and another A/H treatment interval 242 occurs. At the end of this interval (point 250) the patient pressure is at 11 cmH$_2$O, which is the target apnea/hypopnea treatment limit 240.

If another apnea/hypopnea control request is made by A/H monitor 166 at point 250 or at any pressure above the target apnea/hypopnea treatment limit, request processor 106 will still hand over control to A/H controller 168, but A/H controller 168 is prevented from making further increases due to the current patient pressure being at or above the target apnea/hypopnea treatment limit. Instead, A/H controller 168 decreases the patient pressure by a predetermined amount, such as 2 cmH$_2$O to point 252 during a pressure decrease interval 254.

At the end of interval 254, the pressure is either held constant, as indicated by line 256, or is dropped again and held constant, as indicated by line 258. The decision of whether to hold or decrease the pressure from point 252 is made by comparing the current pressure, i.e., the patient pressure at point 252, with the snore treatment pressure. If there is no snore treatment pressure stored in the system, which will be the case if the snore controller has not been activated, the pressure is held at line 256. If there is a snore treatment pressure, and if the current pressure is more than a predetermined amount above this snore treatment pressure, such as more than 2 $cmH_2O$ above the snore treatment pressure, A/H controller 168 will decrease the pressure to a level that is a predetermined amount higher than the snore treatment pressure, and hold it at the lower level, as indicated by line 258, during interval 260. The present invention decreases the pressure to 1 $cmH_2O$ above the snore treatment pressure.

A/H controller 168 maintains the patient pressure constant during interval 260 until a predetermined period of time has elapsed since the start of the pressure decrease, i.e., since point 250. This hold-off period exists in order to allow the patient to stabilize. In a presently preferred embodiment, the pressure is held constant until 15 minutes has expired since the start of the 2 $cmH_2O$ decrease. The present invention contemplates setting the duration of the hold period to other lengths of time, so long as the period of time is sufficient to allow the patient to stabilize. This hold process may be interrupted and reset at any time by a higher level controller. At the end of the 15 minute hold, the target apnea/hypopnea treatment limit is cleared and control is relinquished by A/H controller 160.

H. Variable Breathing Control Layer

The auto-CPAP controller, which is described in the next section, relies on the ability to trend the steady rhythmic breath patterns associated with certain stages of sleep. When a patient is awake, in REM sleep, or in distress, breathing tends to be more erratic and the Auto-CPAP trending becomes unstable. It is, therefore, important to interrupt the auto-CPAP controller if the patient's breathing pattern becomes too variable. In essence, the variable breathing control layer keeps the Auto-CPAP control layer from being too erratic.

Referring back to FIG. 2, the variable breathing control layer, which is assigned a seventh (7th) priority, includes a variable breathing detector 270, a variable breathing monitor 272, and a variable breathing controller 274. As described in greater detail below, the variable breathing control layer performs statistical analysis on the scatter of the trended weighted peak flow data to detect unstable breathing patterns or abrupt changes in patient response. When activated, variable breathing control module 274 takes priority over the auto-CPAP controller, so that when a valid variable breathing indication is provided by variable breathing monitor 272, control of the pressure support system is turned over to the variable breathing controller. In short, activation of variable breathing control module 274 interrupts the operation of the auto-CPAP controller when breathing becomes unstable and appropriately manages any necessary pressure changes.

1. Variable Breathing Detection and Monitoring

Figure 10A:
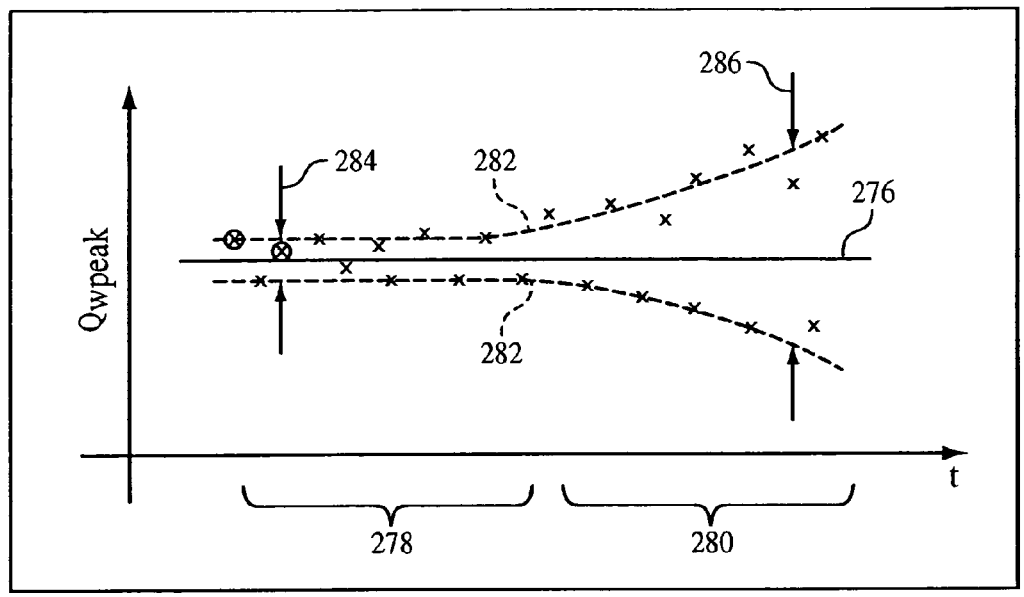
FIGS. 10A and 10B are graphs illustrating the examples of the scatter of weighted peak flows.
Figure 10B:
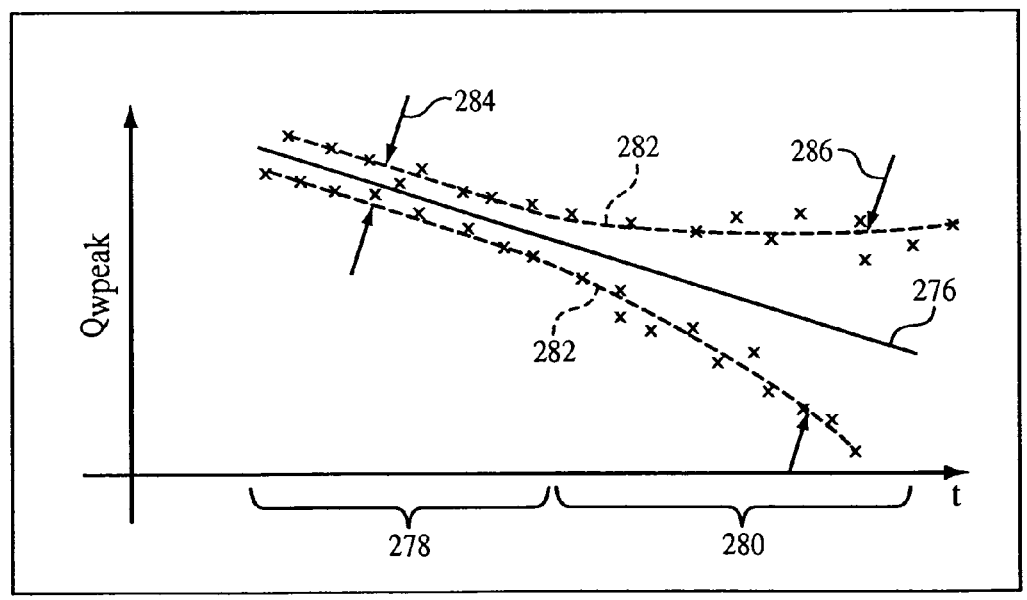

Variable breathing detection module 270 monitors the weighted peak flows $Q_{Wpeak}$ over a moving window, which in a presently preferred embodiment, is a four (4) minute window. The detection module in essence trends four minutes worth of weighted peak flow information to determine whether this information is becoming too erratic. FIGS. 10A and 10B are graphs illustrating examples of the scatter of weighted peak flows. In FIGS. 10A and 10B, the weighted peak flows are relatively closely bunched around a trend line 276 in area 278 and is relatively scattered from the trend line in area 280. Trend line 276 is a best-fit line determined using any conventional statistical analysis technique based on the weighted peak flows data collected during the current 4 minute window. The primary difference between FIGS. 10A and 10B is that the trend line in FIG. 10B is shown with a non-zero slope. This is done to highlight the fact that the trend line is a best-fit line based on the collected data points.

Variable breathing detection module 270 determines the standard deviation of the weighted peak flow data collected during the monitoring window as indicated by dashed lines 282. It should be noted that the standard deviation is calculated based on the best-fit trend line 276. It can be further appreciated that a standard deviation 284 is less in region 278 than a standard deviation 286 in region 280, indicating that the weighted peak flow data is more variable in region 280.

The present inventors appreciated that using the standard deviation alone as a measure of the degree of variation in the weighted peak flow data may not produce consistently correct results. This is so, because the standard deviation of the weighted peak flow data when the mean patient flow is relatively low is not exactly comparable to the same standard deviation for a higher mean patient flow. The present invention, therefore, seeks to normalize the standard deviation to the mean patient flow, and then takes the mean flow into consideration when analyzing the variation in the data.

Figure 11:
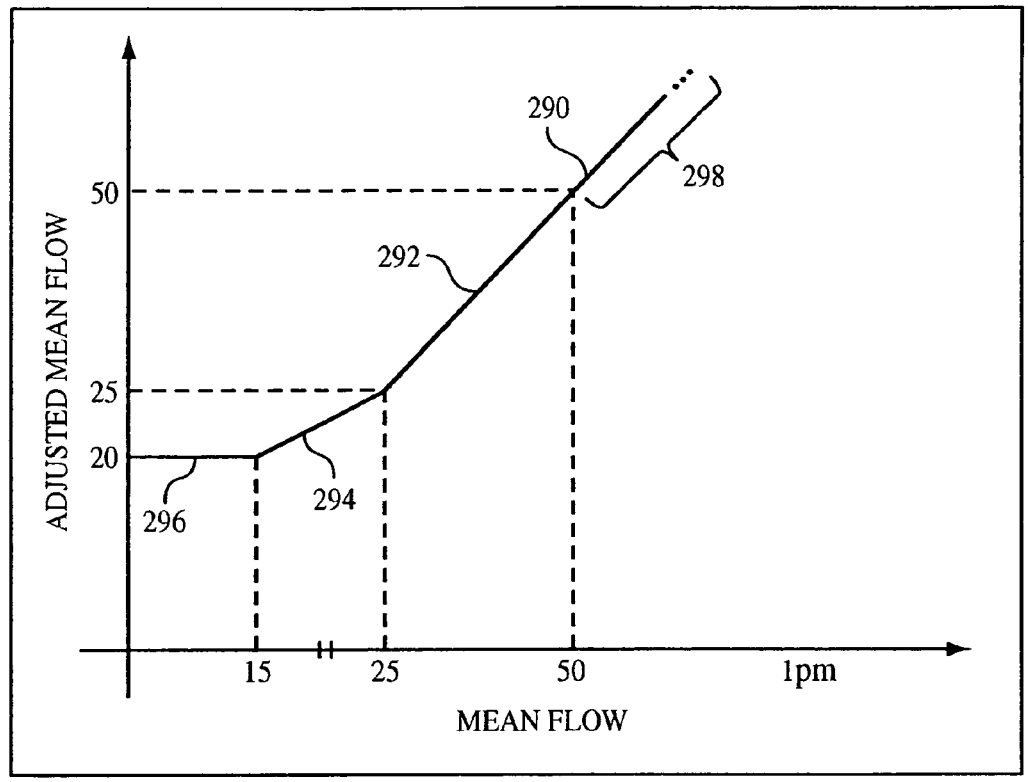
FIG. 11 is a chart illustrating a process by which the mean flow is mapped or normalized according to a variable breathing detection process of the present invention.

FIG. 11 is a chart illustrating a normalization curve 290 that describes the relationship between the mean patient flow and an adjusted mean patient flow. It can be appreciated from reviewing this figure that there is a linear region 292 in which the adjusted mean flow (vertical axis) has a one-to-one match with the actual mean flow (horizontal axis). If the patient's mean flow for the 4 minute window is within region 292, no adjustment to this mean flow is made. There is also a first region 294 having a ½ to one relationship between the adjusted mean flow and the actual mean flow. Thus, if the actual mean flow falls within region 294, which is between 15 and 25 liters per minute (1 pm), then an adjusted mean flow is calculated based on curve 290. There is also a flat region 296 where the adjusted mean flow is clamped to a baseline value even if the actual mean flow is decreased. Thus, if the actual mean flow is less than 15 lpm, the adjusted mean flow is clamped at 20 lpm.

It is to be expressly understood that the specific shape of curve 290 and the delineations between the various regions is subject to variation. For example, although not illustrated, the present invention further contemplates providing this clamping feature if the mean flow exceeds a predetermined value, such as in region 298.

A variable breathing number (VB#) is calculated as follows:

$$VB\# = \frac{\text{standard deviation}}{\text{adjusted mean flow}}. \quad (1)$$

The end result of the variable breathing detection process carried out by variable breathing detection module 270 is this variable breathing number. The higher the VB#, the more variable the weighted peak flow data.

Figure 12:
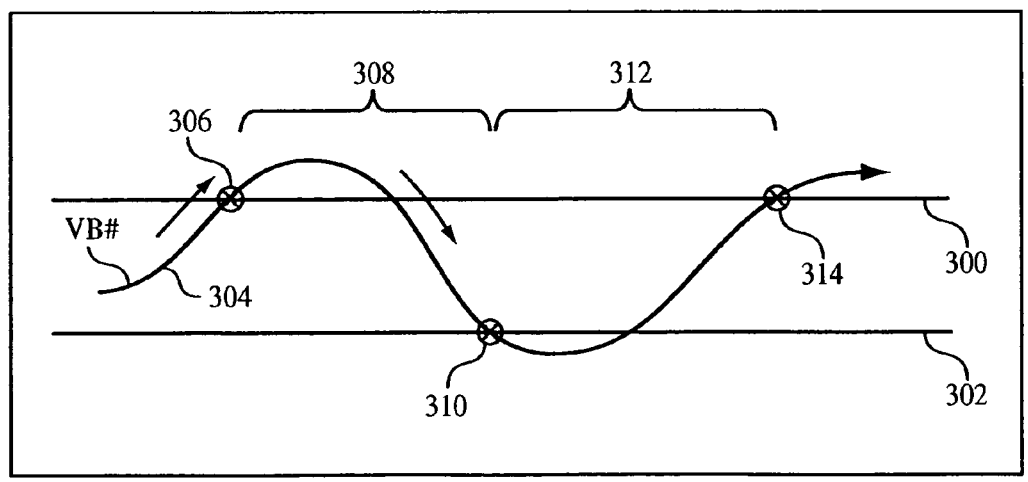
FIG. 12 is a chart illustrating the hysteresis threshold criteria for declaring that the patient is experiencing variable breathing.

The variable breathing number is provided by variable breathing detection module 270 to variable breathing monitoring module 272, which compares this number to threshold values to determine when to request that variable breathing controller 274 take control from the auto-CPAP controller. FIG. 12 is a chart illustrating the hysteresis threshold criteria for declaring that the patient is experiencing variable breathing and, hence for requesting control of the pressure support system.

As shown in FIG. 12, an upper threshold 300 and a lower threshold 302 are set in advance. Preferably, the values of these thresholds are determined from empirical data. Variable breathing monitor 274 declares there to be variable breathing and issues a request for control to request processor 106, when the variable breathing number (VB#), represented by line 304, exceeds upper threshold 300. This occurs at point 306 in FIG. 12. Variable breathing monitor 274 will continue to deem there to be variable breathing, and, hence, continue to request control, even if the VB# falls below upper threshold 300. In short, a variable breathing active indication is turned on at point 306 and remains on over region 308, until the VB# falls below lower threshold 302 at point 310. While the variable breathing active indication is on, variable breathing monitor 274 issues a request for control of the pressure support from request processor 106.

Similarly, variable breathing monitor 274 will continue to deem there to be no variable breathing, and, hence, will not request control, even if the VB# rises above lower threshold 302. That is, the variable breathing active indication is turned off at point 310 and remains off over region 312, until the VB# exceeds upper threshold 300, which occurs at point 314.

2. Variable Breathing Pressure Control

Figure 13:
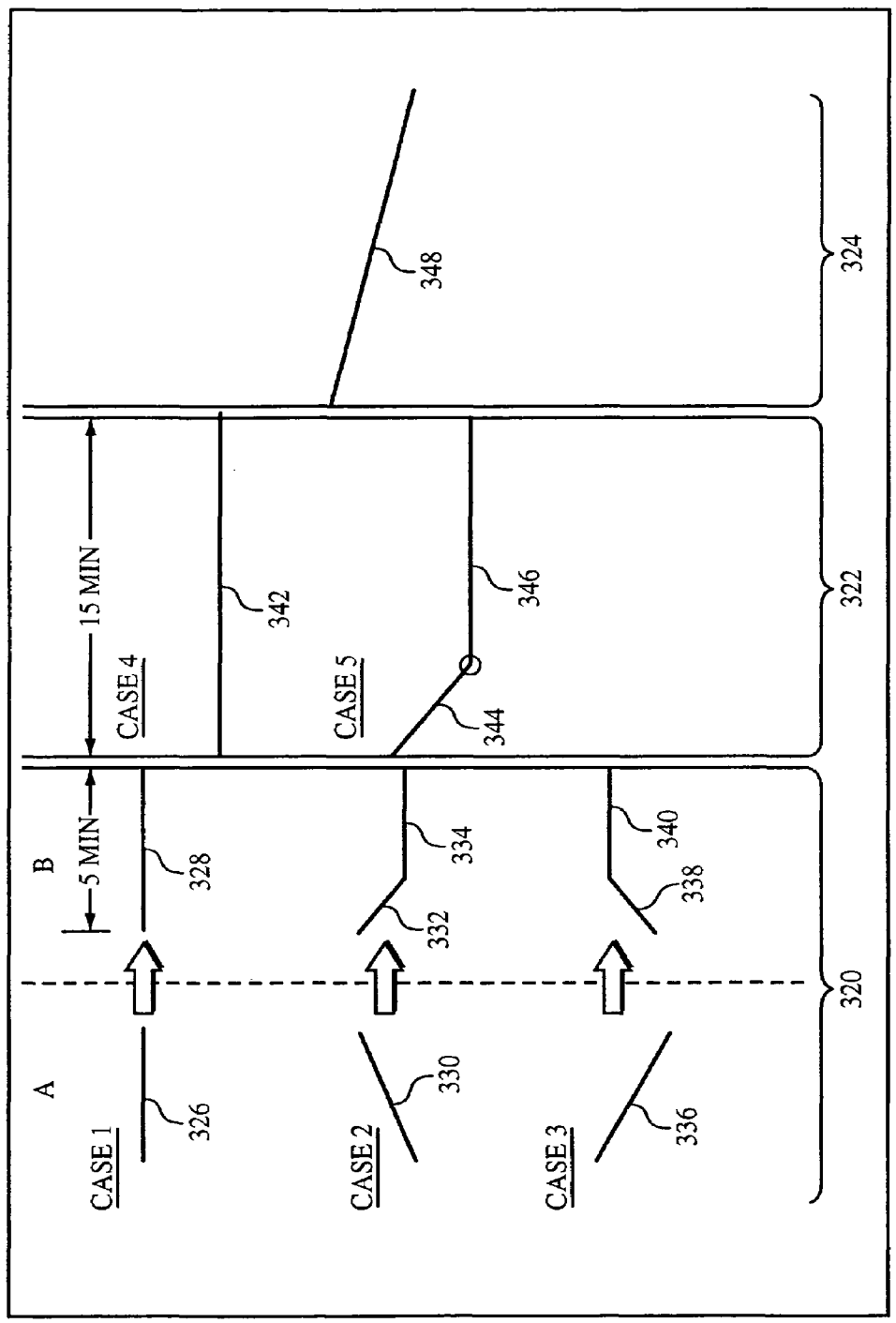
FIG. 13 is a chart illustrating the pressure control operation of the variable breathing control module of the present invention.

Once variable breathing controller 274 has been granted control of the pressure support system, it takes some initial action based on that action the auto-CPAP controller discussed below is taking. After this initial action, it performs an independent pressure control operation. FIG. 13 is a chart illustrating the pressure control operation of the variable breathing control module of the present invention.

As shown in FIG. 13, the pressure control operation performed by variable breathing controller 274 is subdivided into the following three regions: a) an active response region 320, b) a pressure hold region 322, and c) a slow ramp region 324. The pressure control performed by variable breathing controller 274 in each of these regions is discussed in turn below. It is to be understood that even though there appears to be discontinuities in the delivered pressure in FIG. 13, this is only due to the manner in which each region is illustrated. In practice, the pressure at the end of region 320 is the start pressure for the pressure control that takes place in region 322. Similarly, the pressure at the end of region 322 is the start pressure for the pressure control that takes place in region 324.

In region 320, column A illustrates the possible prior pressure curves, i.e., the possible pressure control actions being taken by the pressure support system before operation of the system was handed over to variable breathing controller 274. Column B illustrates the corresponding pressure control curves that are produced by variable breathing controller 274 based on the prior curves. In case #1, a prior pressure 326 is flat (not increasing, not decreasing). In which case, variable breathing controller 274 will cause the pressure delivered to the patient to remain at this level, as indicated by pressure curve 328.

In case #2, a prior pressure 330 is increasing. In which case, variable breathing controller 274 initially decreases the pressure delivered to the patient at a rate of 0.5 $cmH_2O$ per minute, as indicated by pressure curve 332. The magnitude of the decrease is dependent on the magnitude of the increase in prior pressure 330. Pressure decrease 332 is intended to erase the prior pressure increase 330 that possibly caused the variable breathing. However, the total decrease in pressure drop 332 is limited to 2 $cmH_2O$. After pressure decrease 332, variable breathing controller 274 holds the pressure steady, as indicated by pressure curve 334.

In case #3, a prior pressure 336 is decreasing. In which case, the variable breathing controller initially increases the pressure delivered to the patient at a rate of 0.5 $cmH_2O$ per minute, as indicated by pressure curve 338. The magnitude of the increase 338 is dependent on the magnitude of the decrease in prior pressure 336. Pressure increase 338 is intended to erase the prior pressure decrease 336 that may have caused the variable breathing. However, the total increase in pressure 338 is limited to 2 $cmH_2O$. After pressure increase 338, variable breathing controller 274 holds the pressure steady, as indicated by pressure curve 340.

In a presently preferred embodiment, the duration during which pressure is provided according to the paradigms discussed above for region 320, column B, is set to 5 minutes. Thus, pressure curve 328 (case #1) or curve 332–334 (case #2), or curve 338–340 (case #34) is provided for 5 minutes or until the variable breathing condition clears. Thereafter, the pressure is controlled according to the pressure operation of region 322. It is to be understood, however, that this duration can be varied over a range of durations.

In region 322, the pressure is either maintained at a constant value, as indicated by pressure curve 342 (case #4), or it follows a decrease and hold pattern, as indicated by pressure curve 344 (case #5). The decision to hold the pressure (case #4) or to decrease the pressure (case #5) is made by comparing the current pressure, i.e., the patient pressure at the end of region 320, with the snore treatment pressure. This is similar to the pressure control operation of A/H controller 168 discussed above with respect to FIG. 9.

If there is no snore treatment pressure stored in the system, which will be the case if the snore controller has not been activated, the pressure is held constant as pressure curve 342. If there is a snore treatment pressure, and if the current pressure is more than a predetermined amount above this snore treatment pressure, such as more than 2 $cmH_2O$ above the snore treatment pressure, variable breathing controller 274 decreases the pressure to a level that is a predetermined amount higher than the snore treatment pressure, as indicated by pressure curve 344, and holds the pressure at the lower level, as indicated by line 346, over the duration of region 322. The present invention decreases the pressure during pressure decrease 344 to the snore treatment pressure, +1 $cmH_2O$.

In a presently preferred embodiment, the duration during which pressure is provided according to the paradigms discussed above for region 322 is set to 15 minutes. Thus, pressure curve 342 (case #4) or curve 344–346 (case #5) is provided for 15 minutes or until the variable breathing condition clears. Thereafter, the pressure is controlled according to the pressure operation of region 324. It is to be understood, however, that this 15 minute duration can be varied over a range of durations.

In region 324, there is only one pressure control operation. Namely, the pressure delivered to the patient is slowly ramped down, as indicated by pressure curve 348. This downward pressure ramp continues until the minimum system pressure is reached or until the variable breathing condition clears.

I. Auto-CPAP Control Layer

The auto-CPAP control layer is assigned an eighth (8th) and lowest priority from among all of the control layers. As a result, the pressure control operations carried out by this layer are interrupted if any other controller is activated. As shown in FIG. 2, the auto-CPAP control layer includes an auto-CPAP detection module 350, an auto-CPAP monitoring module 352, and an auto-CPAP control module 354.

As will perhaps be better appreciated after reviewing the following discussion of the auto-CPAP control layer, the various components of this layer interact very closely with one another. That is, while the pressure support system is operating in this control layer, the auto-CPAP detector and monitor are continuously analyzing the outputs from monitoring system 44 because the output of the auto-CPAP monitor dictates how the auto-CPAP controller adjusts the pressure at the patient. Unlike the other control layers, there is no need for the auto-CPAP monitoring module to request control from request processor 106, because the auto-CPAP control layer is the default control layer, and will automatically be operating if no other control layer has taken control.

The general goal of the auto-CPAP control layer is to induce slow pressure ramps, e.g., ±0.5 cmH$_2$O/min or to provide a pressure hold period, referred to as a therapy pressure. The patient's response to these pressure changes and to the therapy pressure is evaluated by monitoring certain parameters associated with the flow waveform to determine whether the patient flow waveform is improving, degrading, or showing no change. For each breath, values are calculated representing the weighted peak flow $Q_{Wpeak}$, roundness, flatness, and skewness of that breath. This data is stored and trended over time in a continuous effort to optimize the pressure delivered to the patient by the pressure support system.

1. Peak, Roundness, Flatness and Skewness

As noted above, during the auto-CPAP control process carried out by auto-CPAP controller, the weighted peak flow $Q_{Wpeak}$, roundness, flatness, and skewness of the inspiratory waveform for a breath are determined. Each of these characteristics of the inspiratory waveform are trended over time by auto-CPAP detector 350 to produced a trended value. This trended value is provided to auto-CPAP monitoring module 352, where it is used in a voting scheme discussed in greater detail below to determine what action the auto-CPAP controller takes. Therefore, it is important to understand first how the present invention calculates these inspiratory waveform characteristics.

The calculation of the weighted peak flow $Q_{Wpeak}$ was discussed above with reference to A/H detection module 164. Therefore, no further explanation of this inspiratory waveform characteristic is required.

Figure 14A:
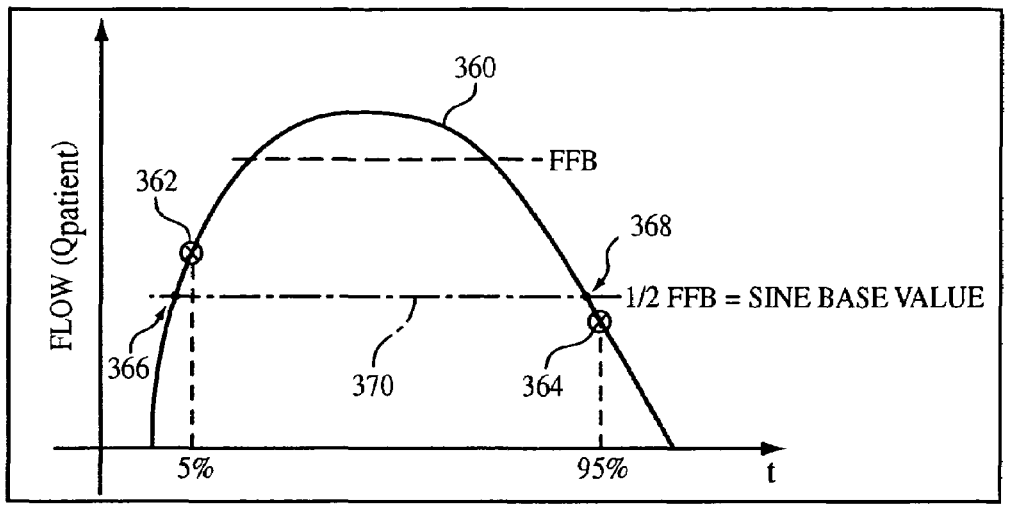
FIGS. 14A–14C illustrate exemplary patient inspiratory waveforms for use in explaining the roundness and flatness calculations of the present invention.
Figure 14B:
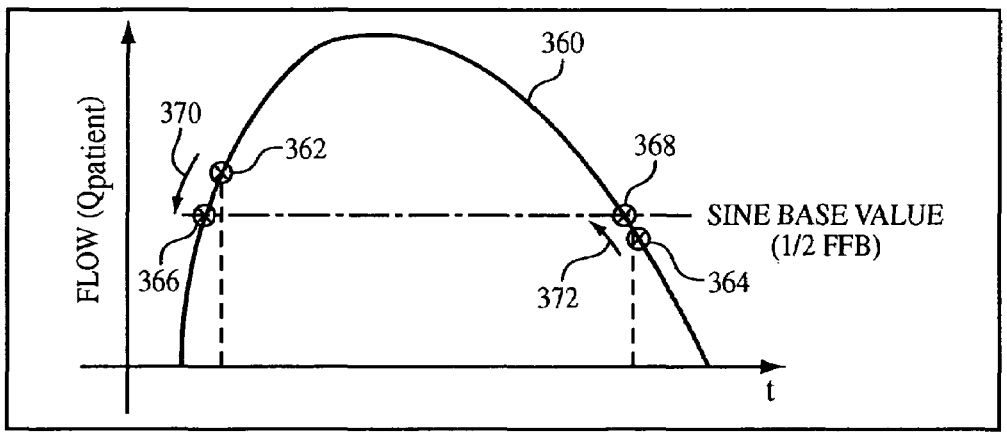
Figure 14C:
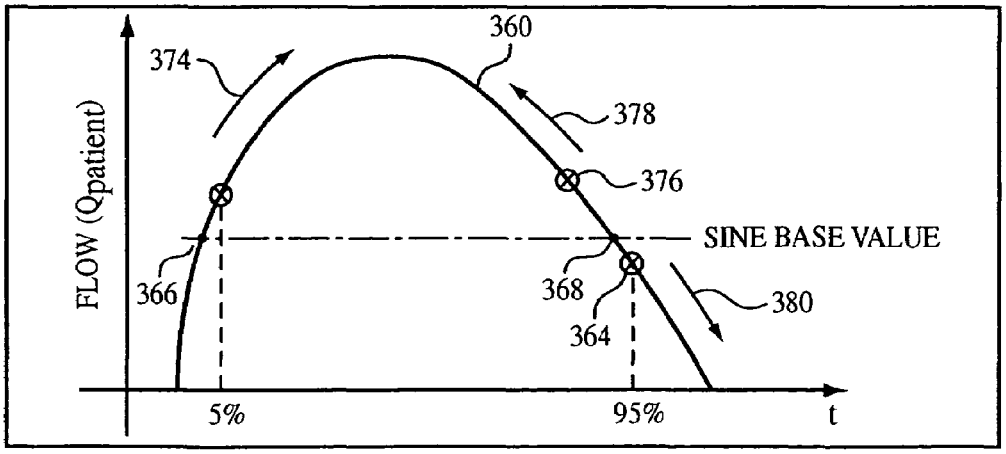

In order to calculate the roundness characteristics of the inspiratory waveform, the present invention compares a patient's inspiratory wave to a sine wave. FIGS. 14A–14C illustrates an exemplary patient inspiratory waveform 360 including points 362 and 364 on this waveform that corresponds to the 5% and 95% volumes, respectively. Comparing waveform 360 to a sine wave requires matching the patient's inspiratory wave to the sine wave, or vice versa, in order to make the best possible comparison. For this reason, several steps must be taken in order to fit the sine wave onto the patient's inspiratory waveform.

First, a sine base value, which is used to place the start and end points of a sine wave on patient's inspiratory waveform 360 is calculated. The sine base value is defined as ½ of the flatness flat baseline (FFB) value. Points 366 and 368 where line 370, which is a line corresponding to the sine base (½FFB), intersects inspiratory waveform 360 are selected as a start point and an end point of the sine wave to be overlaid on the inspiratory waveform. The task then becomes locating points 366 and 368 on waveform 360.

The present invention locates these points by searching for the points on the inspiratory waveform beginning from a known landmark value, such as the 5% volume point 362 and the 95% volume point 368. As shown in FIG. 14B, when searching at the start or proximal end of the inspiratory waveform, if the flow value for the 5% volume (point 362) is less than the sine base value, search up, i.e., toward a distal end of waveform 360, i.e., where the 95% volume point is located. On the other hand, if the flow value for the 5% volume (point 362) is greater than the sine base value, search down, i.e., toward the proximal end or beginning of waveform 360. Arrow 370 in FIG. 14B indicates a downward search from the 5% volume point toward the proximal end of the waveform, because, in this exemplary embodiment, the flow at point 362 is greater than the sine base value.

When searching at the distal end of the inspiratory waveform, if the flow value for the 95% volume (point 364) is greater than the sine base value, search up, i.e., toward the distal end of waveform 360. On the other hand, if the flow value for the 95% volume (point 364) is less than the sine base value, search down, i.e., toward the proximal beginning of waveform 360 where the 5% volume point is located. Arrow 372 in FIG. 14B indicates a downward search from the 95% volume point, because, in this exemplary embodiment, the flow at point 364 is less than the sine base value.

In searching for the location of the points on waveform 360 that correspond to the sine base value, it can happen that a search beginning at a landmark, such as the 5% volume point, fails to find the correct point on waveform 360 that should correspond to the start of the sine wave. For example, if point 362 is above the sine base value point and the searching is done upward, as indicated by arrow 374 in FIG. 14C, the search for the start point may erroneously locate point 368, which is near the end of the inspiratory waveform, as the start point. A similar error would occur if the 95% point is greater than the point corresponding to the sine base value, shown as exemplary point 376, and a downward search was done from point 376, as indicated by arrow 378.

To avoid these errors, the present invention includes validity checks to see if the search (arrows 374 and 376) crossed one another. If so, the points found by each search are discarded and no calculation of roundness and flatness are made for that waveform. A similar error and result occurs if no point is found that corresponds to the sine base value. This can occur, for example, if upward searching begins at point 364, as indicated by arrow 380.

Figure 15:
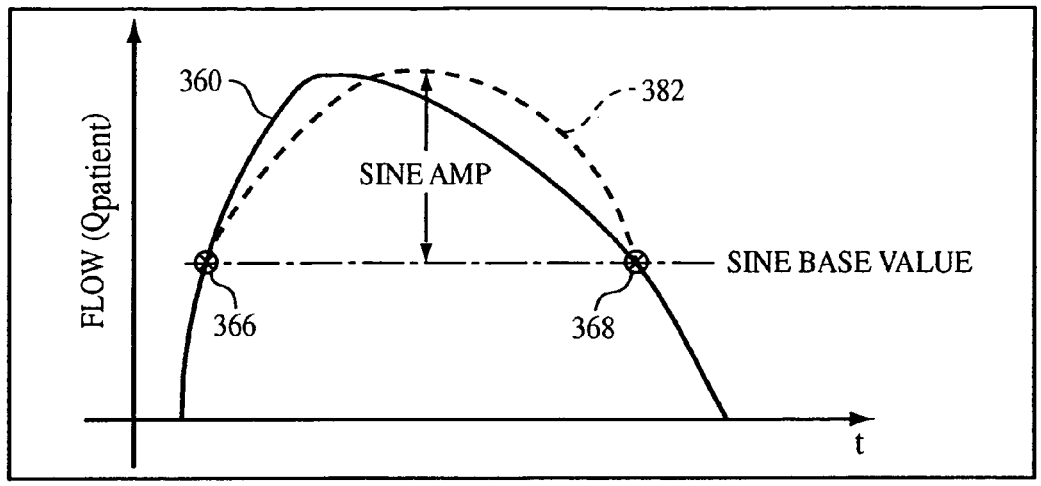
FIG. 15 illustrates an exemplary patient inspiratory waveform and a sine wave template for use in explaining the roundness and flatness calculations.

Once start point 366 and end point 368 for a sine wave template 382 in FIG. 15 are known, the amplitude (Sine Amp) of sine wave template 382 having these start and end points is calculated using the known relationship between the width or period of a sine wave and its amplitude. See FIG. 15. For example, the Sine Amp is calculated as:

$$\text{Sine Amp} = \frac{\int_{Start\ point}^{End\ point} Q_{patient}(t)}{2\pi}. \quad (2)$$

From the known period of the sine wave, i.e., the time between the start and end points, and the calculated amplitude, the present invention then determines a ratio of amplitude over period. In other words, a ratio is calculated as:

$$\text{Ratio} = \frac{\text{Sine Amp}}{\text{Period}}. \quad (3)$$

Figure 16A:
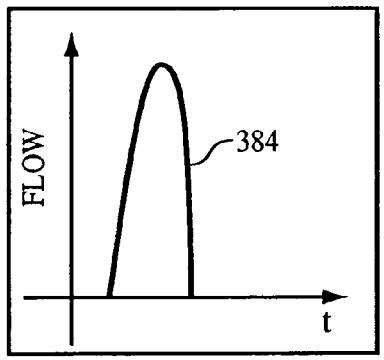
FIGS. 16A and 16B illustrate extreme examples of different sine wave templates.
Figure 16B:
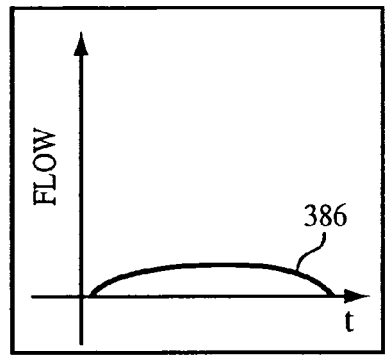

The purpose of determining this ratio is to attempt to normalize the sine wave templates to one another by adjusting the amplitude of the sine wave templates. For example, if the ratio is very high, it indicates that the sine wave template 384 is very tall and thin, as shown, for example, in FIG. 16A. If the ratio is very low, the sine wave template 386 is very short and wide, as shown, for example, in FIG. 16B. It is preferable not to compare these tall, thin templates 384 or short, wide templates 386 to the actual patient inspiratory waveform because the fit between these two wave patterns is typically not very good and does not produce meaningful results.

Figure 17:
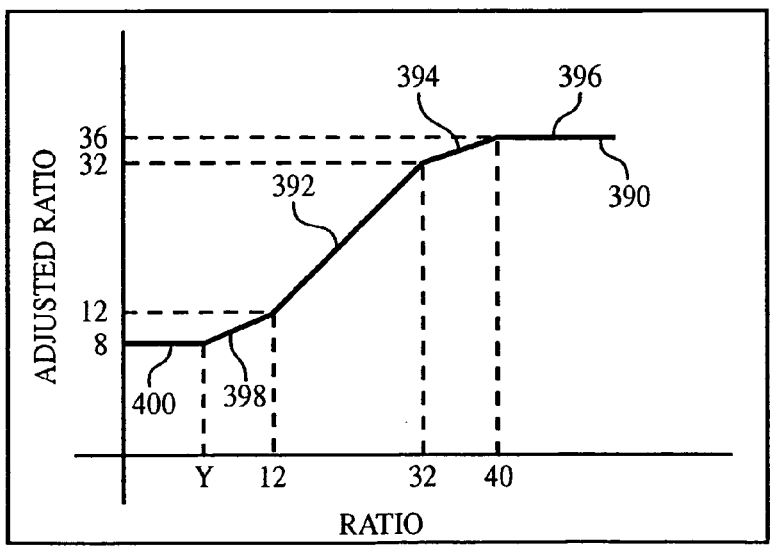
FIG. 17 illustrates a normalization curve that is used to adjust the ratio of the sine wave templates.

To account for these conditions, the present invention adjusts the ratio of the sine wave template. FIG. 17 illustrates a normalization curve 390 that is used to adjust the ratio of the sine wave templates. Normalization curve 390 includes a linear region 392 where no ratio adjustment is made. Above linear region 392, i.e., where the sine wave template has a ratio that is too high, normalization curve 390 includes a first region 394 that downwardly adjusts the ratio and a clamping region 396. In the illustrated exemplary embodiment, the adjusted ratio is clamped at 36, no matter how high the actual ratio is. Below linear region 392, i.e., where the sine wave template has a ratio that is too low, normalization curve 390 includes a second region 398 that upwardly adjusts the ratio and a clamping region 400. In the illustrated exemplary embodiment, the adjusted ratio is clamped at 8 no matter how low the actual ratio is.

Figure 18A:
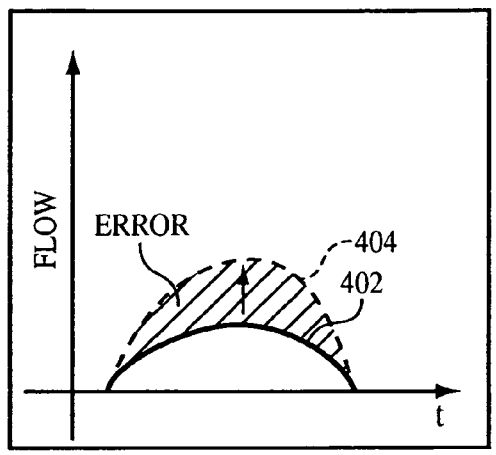
FIGS. 18A and 18B illustrate sine wave templates showing how the amplitude of the template is corrected according the roundness and flatness calculation process of the present invention.
Figure 18B:
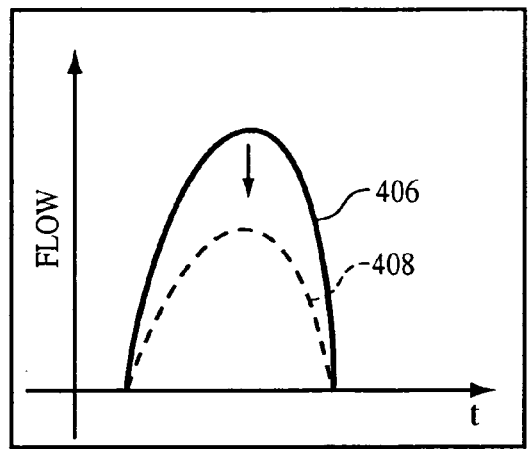

The adjusted ratio determined from the relationship shown, for example, in FIG. 17, is used to set the amplitude of the sine wave template, with the period being held constant. For example, FIG. 18A illustrates a sine wave template 402 where the ratio is too low, meaning that the sine wave template is too flat. A corrected sine wave template 404 is also shown indicating how adjusting the ratio effectively increases the amplitude of the sine wave template. FIG. 18B illustrates a sine wave template 406 where the ratio is too high, meaning that the sine wave template is too tall. A corrected sine wave template 408 is also shown indicating how adjusting the ratio effectively decreases the amplitude of the sine wave template.

After the sine wave template that corresponds to the patient's inspiratory flow is determined and corrected, if necessary, the volume of the corrected sine wave template is calculated using any conventional technique. In an analog computation, this is accomplished by integrating over the corrected sine wave template from the start point to the end point. In a digital process, this is accomplished by summing the flows from the start point to the end point and dividing by the number of summations in this process.

Figure 19A:
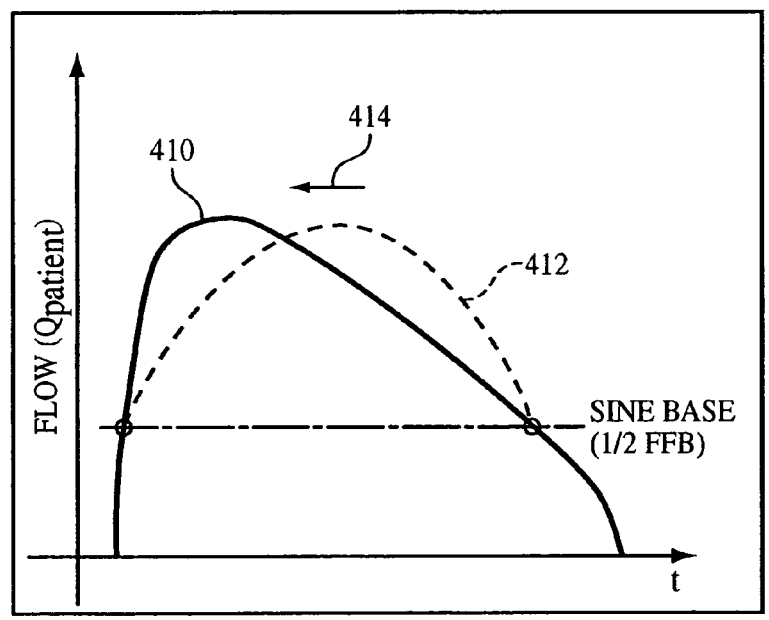
FIGS. 19A and 19B illustrate an exemplary patient inspiratory waveform and a corresponding sine wave template for use in explaining the roundness and flatness calculations.
Figure 19B:
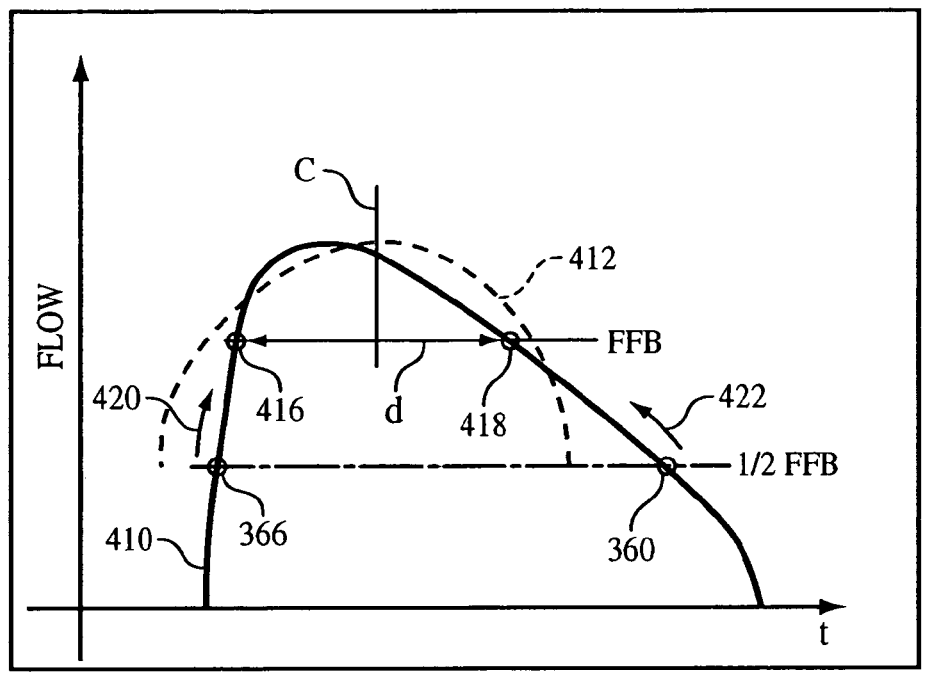

FIG. 19A illustrates an exemplary patient inspiratory waveform 410 and a sine wave template 412 determined as discussed above. It can be appreciated from reviewing this figure that there remains a relatively large degree of offset between patient inspiratory waveform 410 and a sine wave template 412. The present invention accounts for this offset by effectively shifting the sine wave template, as indicated by arrow 414, to overlie the patient inspiratory waveform.

In a preferred embodiment of the present invention, shifting the template to overlie the patient inspiratory waveform is accomplished by determining a center C of the patient inspiratory waveform and using this center as a new center for the sine wave template. Center C of patient inspiratory waveform 410 is determined by finding the points 416 and 418 on the inspiratory waveform that corresponds to the FFB value. Finding the points 416 and 418 on the inspiratory waveform that corresponds to the FFB value is accomplished by searching up or down from the known landmark points 366 and 368, which correspond to the sine base value (½FFB). This search is indicated by arrows 420 and 422. Once the FFB points are located on inspiratory waveform 410, the center C of the inspiratory waveform is taken as ½ the distance between these FFB points (416 and 418). Now that center C of inspiratory waveform is located, the location points defining sine wave template 412 can be recalculated about this center.

Figure 20:
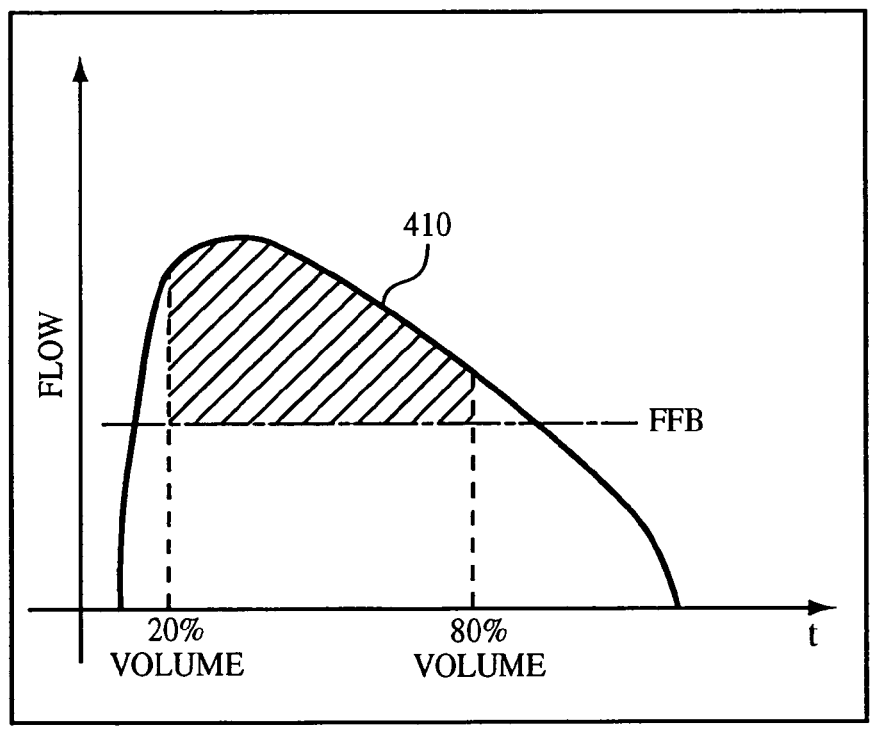
FIG. 20 illustrates a patient inspiratory waveform showing how flatness is calculated according to the principles of the present invention.

Referring now to FIG. 20, a flatness level is calculated by determining the volume of the inspiratory waveform 410 above the flatness flat baseline (FFB) level between the 20% volume point and the 80% volume point. Preferably, a weighting constant is applied to this result to make it less sensitive to slight changes in the shape of the inspiratory waveform.

In a digital processor, flatness can be determined as follows:

$$\text{Flatness} = \frac{4*100*\sum_{20\%\ Volume}^{80\%\ Volume} \text{abs}(Q_p(t) - \text{Flatness Flat Baseline})}{T_{20\%-80\%} * \text{Flatness Baseline}}. \quad (4)$$

In this relation, the constant value 4 is the weighting constant that makes this determination less sensitive to changes in the shape of the inspiratory waveform. Constant value 100 is selected so that the flatness value is expressed as a percentage. Interestingly, the flatness value is large when the inspiratory waveform is sinusoidal and could be zero if the inspiratory waveform is perfectly flat.

Figure 21:
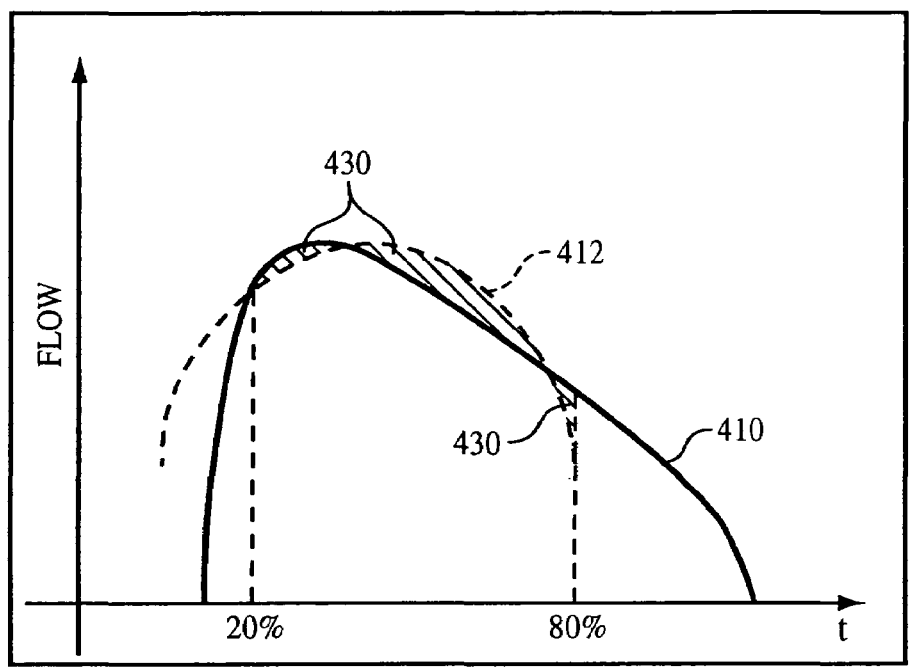
FIG. 21 illustrates a patient inspiratory waveform showing how roundness is calculated according to the principles of the present invention.

Referring now to FIG. 21, roundness is calculated as the difference between a patient inspiratory waveform 410 and the sine wave template 412 determined as discussed above between the 20% volume point and the 80% volume point. This difference is shown in FIG. 21 as shaded areas 430. A weighting constant is preferably also applied to the roundness determination to make it less sensitive to slight changes in the shape of the inspiratory waveform.

In a digital processor, roundness can be determined as follows:

$$\text{Roundness} = \frac{2*100*\sum_{20\% \text{ Volume}}^{80\% \text{ Volume}} \text{abs}(\text{Flow Sine}(t) - Q_p(t))}{\text{Sine Volume}}, \quad (5)$$

Interestingly, the roundness value is large when the inspiratory waveform is flat and could be zero if the inspiratory waveform is a perfect sinusoid.

Figure 22:
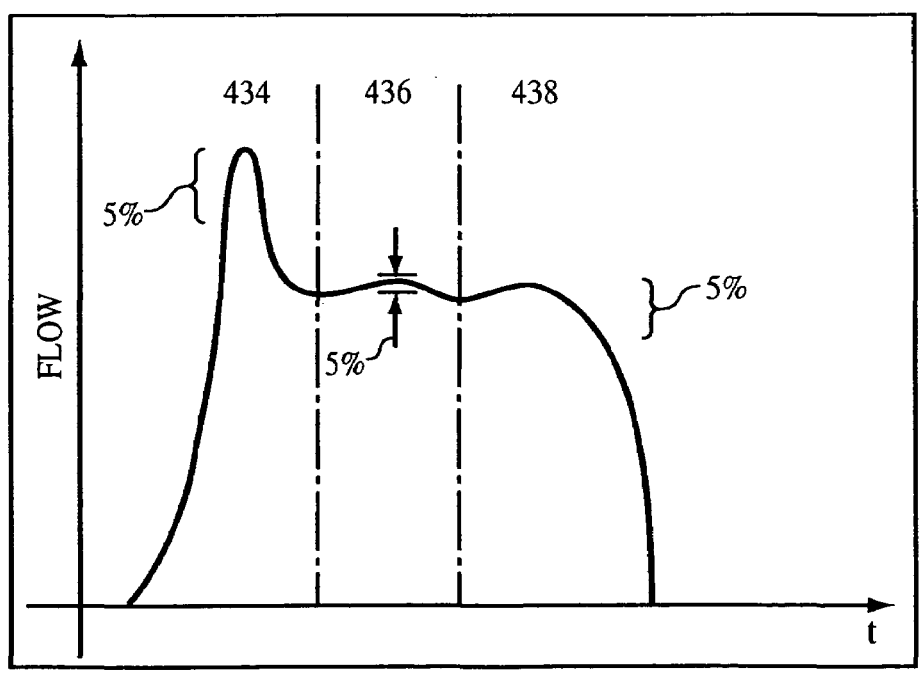
FIG. 22 illustrates a patient inspiratory waveform showing how skewness is calculated according to the principles of the present invention.

Referring now to FIG. 22, skewness is calculated by first segmenting an inspiratory waveform 432 into regions 434, 436 and 438. Each region corresponds to ⅓ of the duration of the inspiratory waveform. A predetermined amount of the top flows in each region is averaged. For example, in a preferred embodiment of the present invention, the top 5% of the flow in each region is averaged. A skewness number for the inspiratory waveform is calculated as the 5% of the middle region 436 divided by the 5% of the left region. Stated another way, the skewness number is calculated as:

$$\text{Skewness Number} = \frac{\text{Middle Region 5\%}}{\text{Left Region 5\%}}. \quad (6)$$

It can be appreciated that the specific manner in which the inspiratory waveform is segmented, and the percentage of flow from each that are analyzed to determine the skewness value are subject, to variation.

2. Auto-CPAP Detection Module

Auto-CPAP detection module 350 performs two types of trend analysis on each of the monitored breath parameters, i.e., weighted peak flow, flatness, roundness, and skew data collected over any period of time, which is typically 2.5 to 20 minutes. The first is a long-term trend analysis, and the second is referred to as a short-term trend analysis. However, each type of trend analysis requires first collecting the data for the analysis. Naturally, as more data is input into the trend analysis, the more likely the analysis will be representative of the patient's response.

Figure 23:
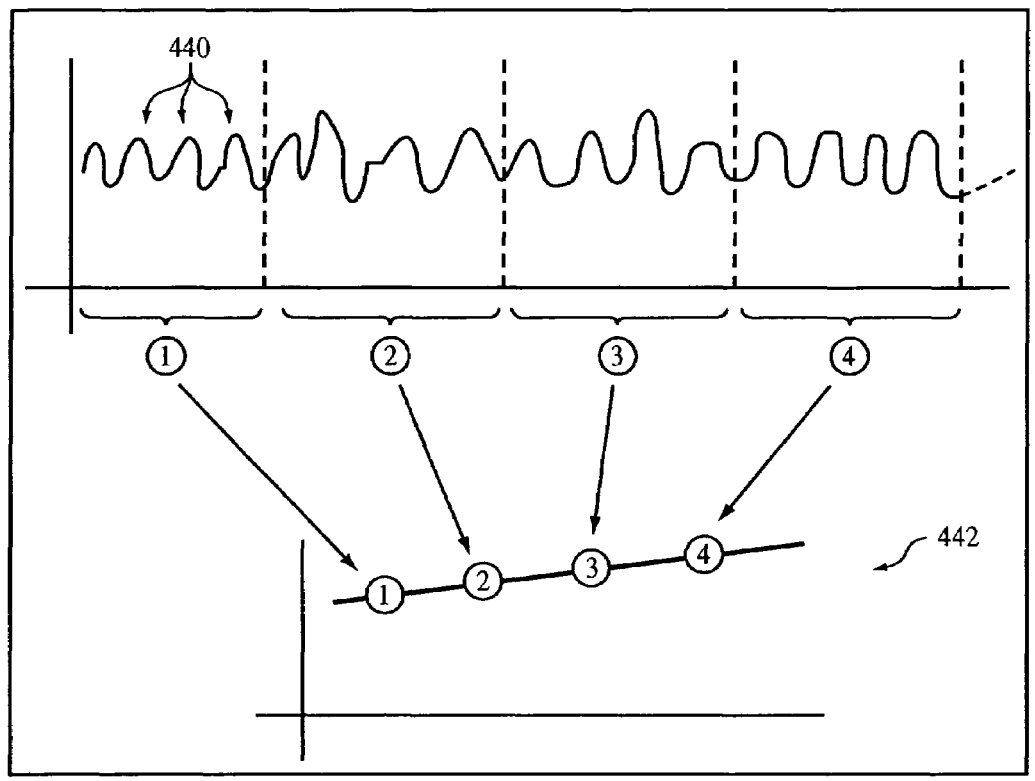
FIG. 23 illustrates how respiratory parameter data is accumulated for trend analysis purposes according to the principles of the present invention.

As shown in FIG. 23, the breath parameter data for a patient's breathing cycles 440 are grouped into sets, with each set containing the data associated with multiple breathing cycles. In a presently preferred embodiment, each set includes respiratory parameter data for four breathing cycles.

The respiratory or breath parameters, i.e., weighted peak flow $Q_{Wpeak}$, roundness, flatness, and skewness, for each breath are calculated as discussed above. The weighted peak flow data for four breaths, for example, are averaged and used to determine a single point value for use in the trend analysis. This same process is conducted for the other respiratory parameters of roundness, flatness, and skewness. The result is an accumulation of data, as indicated by chart 442, that is used for trend analysis purposes.

Figure 24:
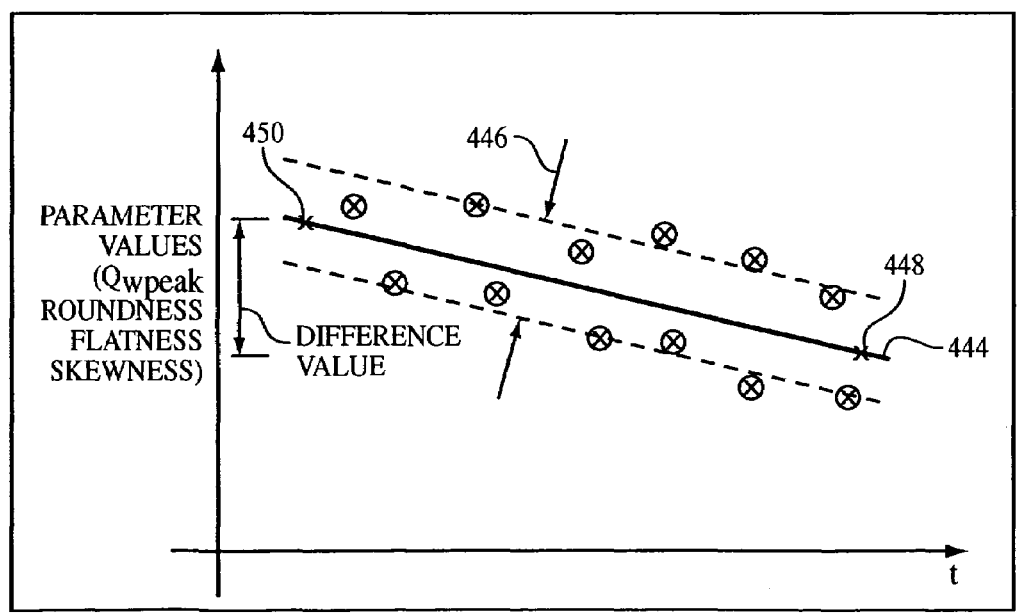
FIG. 24 is a chart illustrating the trend analysis technique of the present invention.

FIG. 24 illustrates an exemplary trend analysis chart, where each point represents the averaged respiratory parameter data over four breathing cycles. Trend analysis of this data involves determining a least squares fit line, also referred to as a best-fit line, 444 for the data points. It can be appreciated that the slope of best-fit line 444 is indicative of the degree with which the trend of the data is changing.

Next, a standard deviation 446 of the data points about this best-fit line is determined over the time interval of interest.

A variety of different types of analysis can be done based on this data. For example, the present invention contemplates determining a percent change and a difference value of the trend data. The percent change is calculated as:

$$\% \text{ change} = \frac{\text{end point} - \text{start point}}{\text{mean}} \times 100, \quad (7a)$$

where the end point is a point on best-fit line 444 near the end of the collected data, such as point 448, the start point is a point on best-fit line 444 near the start of the collected data, such as point 450, and the mean is the mean value of the data points between the start and end points. An equivalent calculation for the percent change can be expressed as:

$$\% \text{ change} = \frac{\text{slope} \times \text{trend length}}{\text{mean}} \times 100, \quad (7b)$$

where slope is the slope of the best-fit line 444 and the trend length is the length of the trend, indicated as the time between the start point and the end point.

The difference value is calculated as the difference between the value of the end point and the start point expressed as:

difference value=end point−start point. (7c)

The equivalent representation of this equation can be expressed as:

difference value=slope×trend length. (7d)

According to a preferred embodiment of the present invention, when analyzing the weighted peak flow data, only the percent change is used. When analyzing the roundness, flatness, and skewness data, only the difference value of the trend data is used because, in a preferred embodiment of the present invention, these raw measures are already represented as percentages. An error window, defined by a percent change or difference as described above, is compared to predetermined thresholds to determine whether the change in the data, i.e., the trend, has exceeded acceptable levels. It should be noted that the type of analysis (percent change or difference) depends on the type of raw data used in the trends analysis.

As noted above, auto-CPAP detection module 350 looks at a short-term trend and a long-term trend of the accumulated data points—recall that each data point contains an average of the parameter data for four breathing cycles. When performing the long-term trend analysis, the percent change or the difference value (depending on the parameter of interest) is evaluated over time to determine whether these trend analysis criteria fall outside predetermined thresholds. When performing the short-term trend, each newly collected data point is compared to the data points already collected in an effort to locate anomalies in the monitored parameters relative to the trended data.

a. Long-Term Trend

To perform the long-term trend analysis, the best-fit line for the trended data, which has an associated standard deviation for the data points around that line, is used to determine a trend error window. The trend error window represents a range of error for the trend data. The trend error window is a function of the standard deviation for that best-fit line, the number of data points used in the trend calculation, and the desired confidence level, and is determined using any conventional technique, such as using a look-up table, once the input criteria (standard deviation, # of samples (data points), and confidence level) are established.

In the present invention, the confidence level used in selecting the trend error window is determined based on an empirical evaluation of the data. It was determined from this empirical analysis that, for purposes of the present invention, an 80% confidence level is appropriate for the trend error window. However, those skilled in the art can appreciate that this level can be varied and still provide meaningful results. In essence, in selecting an 80% confidence level, the present invention seeks to say, with an 80% level of confidence, that the best-fit line, with its associated scatter of data, represents the true trend of the data being analyzed.

Once a trend error window is determined, this range of error is converted into an error window based on the difference value or the percent change discussed above. This can be accomplished by applying the calculations discussed in equations (7b) and (7d) to the trend error window. In this case, the slope of the best-fit line would be represented by a range of slopes that take into account the best-fit line 444 and its associated trend error. Once the error window is converted to a difference or percent change, it is provided from auto-CPAP detector 350 to auto-CPAP monitor 352, which uses this trend based information, as discussed below, to judge the patient's response changes to the delivered pressure.

b. Short-term Trend

The short-term trend analysis attempts to distinguish relatively quick patient response to the delivered pressure. Therefore, rather than looking at the changes in the trend data over time, the short-term trend analysis function of auto-CPAP detection module 350 in combination with auto-CPAP monitoring module 352, analyzes each data point as it is generated against two detection criteria. The auto-CPAP detection module establishes the short-term trend criteria, and the auto-CPAP monitoring module 350 analyzes the newly generated data point against these criteria.

The first short-term trend criteria determined by the auto-CPAP detection module is a prediction interval. The goal of the prediction interval is to provide a range of values against which the newly generated data point is compared. The prediction interval is determined, using standard statistical analysis techniques, based on the standard deviation of the data points about the best-fit line, the number of samples or data points in the trend analysis calculation, and the desired confidence level. In the present invention, the confidence level used to select the prediction interval is determined based, on an empirical evaluation of the data. It was determined from this empirical analysis that, for purposes of the short-term trend analysis, a 95% confidence level is appropriate. However, those skilled in the art can appreciate that this level can be varied and still provide meaningful results. Based on these criteria, the prediction interval represents a range of values in which we are 95% confident that the next generated data point will fall within this range of values.

The second short-term trend criteria determined by the auto-CPAP detection module is simply a "start of trend data point," which is a data point on the best-fit line at the start of the collection of data. The start of trend data point is similar to data point 450 in FIG. 24. As previously described for the long-term trend, a percent change and difference is calculated for the short-term. This is accomplished by using equations (7a) and (7c) described above. For the short-term calculation, the end point is defined as the value of the current data point, and the start point is defined as the start of trend point, similar to data point 450 in FIG. 24. As discussed below, the prediction interval and the short-term percent change (or difference, i.e., dependent upon the individual breath measure, consistent with that described for the long-term trend) are provided from auto-CPAP detection module to auto-CPAP monitoring module 352.

3. Auto-CPAP Monitoring Module

Auto-CPAP monitoring module 352 uses the trend information provided by auto-CPAP detection module 350 in a voting process to determine the patient's response to a pressure being delivered to the airway. For example, the auto-CPAP monitor determines whether or not the profile of the patient flow waveform is improving or degrading, thus indicating whether airway flow restriction may be improving or degrading.

a. Long-Term Trend Voting

Figure 25:
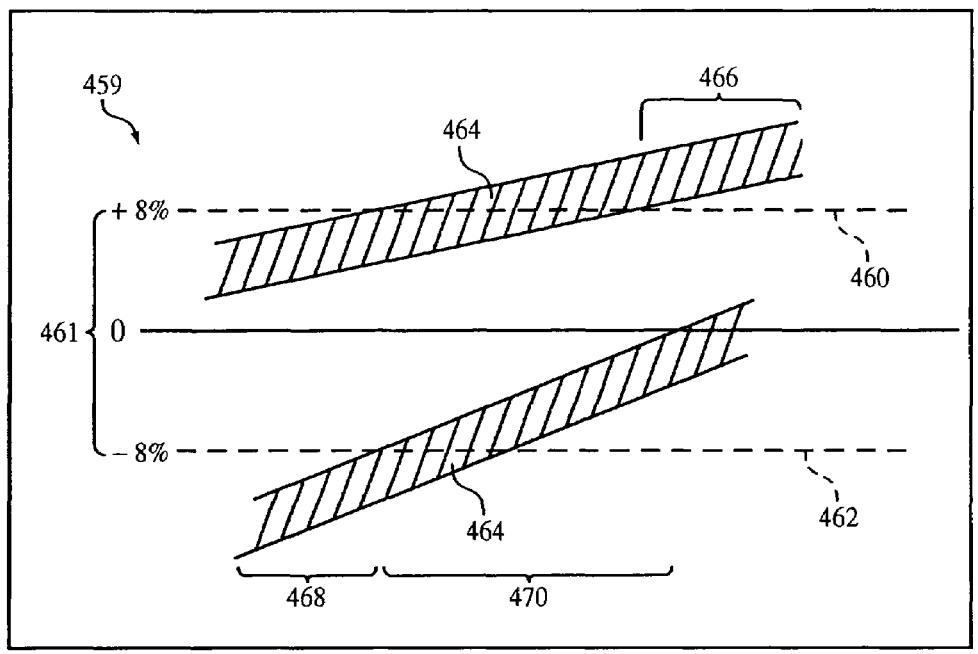
FIG. 25 is a chart explaining the voting process carried out during a long-term trend analysis according to the present invention.

FIG. 25 is a chart 459 explaining, by illustration, the voting conducted on the information provided by the long-term trend analysis. At the center of chart 459 is a voting window 461 that is bounded by an upper threshold 462 and a lower threshold 464. There are three levels of voting in this chart: 1=getting better, 0=no change, −1=getting worse.

The trended data, along with its associated statistical error, which corresponds to an error window 464 calculated during the long-term trend analysis performed by the auto-CPAP detector, is compared to thresholds 460 and 462. In order to produce a vote of 1, the entire error window must exceed an assigned threshold level. This threshold level varies from measure to measure, but typically ranges from 7% to 8%. In FIG. 25 the 8% value is selected. If the entire error band 464 is above threshold level 460, a vote of 1 is generated, as indicated by region 466. Similarly, if the entire error band 464 is below threshold level 462, as indicated by region 468, a vote of −1 is generated. Otherwise a vote of zero (0) is generated, region 470.

b. Short-Term Trend Voting

The short-term trend analysis described above and the short-term voting scheme described below is designed to detect short-term or relatively sudden changes in the patient's flow profile. This is accomplished by comparing a single grouping of breaths (i.e., one data point, which contains 4 breaths) to the first and second short-term trend criteria discussed above and to determine whether that group has shown a statistically significant change with regard to the long-term trended data.

If (1) the newly generated data point is equal to or outside the prediction interval and (2) the data point differs from the start of trend data point by a predetermined threshold amount, the data point (i.e., breath group) is deemed to represent a significant change with respect to the beginning of the long-term trend. Therefore, if both of these conditions are met, the short-term trend generates a vote of 1 or −1, depending on whether the data point is above or below the start of trend data point. Otherwise, a vote of zero (0) is generated. The threshold for the percent change or difference between the data point and the start of trend data point used for short-term trending varies from measure to measure, but typically ranges from 9% to 14%.

c. Final Voting

Once a long-term vote and a short-term vote has been issued for each individual breath measure, the votes from all the measures are then accumulated into a single, final vote. The following table summarizes the final voting process:

|  | Long-Term Vote | Short-Term Vote | Result |
|---|---|---|---|
| $Q_{Wpeak}$ | (−1, 0, 1) | (−1, 0, 1) | a |
| Roundness | (−1, 0, 1) | (−1, 0, 1) | b |
| Flatness | (−1, 0, 1) | (−1, 0, 1) | c |
| Skewness | (−1, 0, 1) | (−1, 0, 1) | d |
|  |  | Final Vote | x = a + b + c* + d |

The value placed in the "Result" column for each breath parameter is the value of the long-term vote, unless the long-term vote is zero. If the long-term vote is zero, the-short-term vote value is placed in the results column for that breath parameter. The results are summed to generate the final vote.

The only other caveat implemented by the present invention is that the flatness breath parameter is ignored when summing for the final vote if the flatness result is non-zero and if it is inconsistent with the other non-zero voting breath parameters associated with the shape of the inspiratory waveform, i.e., roundness and skewness. This is why an asterisk is placed next to "c" in the above table, meaning that in certain situations the flatness value "c" is ignored. For example, the result for flatness is 1, and either the roundness or the skewness parameter is a −1, the flatness result is ignored in the summation for the final vote. Similarly, if the result for flatness is −1, and the either the roundness or the skewness parameter is a 1, the flatness result is ignored in the summation for the final vote.

The final vote "x" from the above table can have a range of −4 to 4 and is used to determine the three primary conditions about the profile of the patient flow waveform. The condition of the patient's inspiratory flow is also indicative of the patient's response to the pressure being provided to the airway. The three primary conditions that summarize a patient's response to the pressure, and the final vote value associated with each condition, are given below:

1) statistically significant degradation, $x \leq -2$
2) statistically no change, and $-2 < x < 2$
3) statistically significant improvement. $x \geq 2$ All three of these conditions can be determined independent of whether the auto-CPAP controller is increasing, decreasing, or holding pressure constant. The following table summarizes where each condition (1), (2) or (3) falls for each value of x:

| x = −4 | x = −3 | x = −2 | x = −1 | x = 0 | x = 1 | x = 2 | x = 3 | x = 4 |
|---|---|---|---|---|---|---|---|---|
| (1) | (1) | (1) |  |  |  |  |  |  |
|  |  |  | (2) | (2) | (2) |  |  |  |
|  |  |  |  |  |  | (3) | (3) | (3) |

As discussed in greater detail below, during certain pressure control operations performed by auto-CPAP controller 354, a fourth condition, which is interposed between conditions (2) and (3), is added. This additional condition, which is designated as condition (2.5) because it is between conditions (2) and (3), corresponds to the patient condition, i.e., the patient inspiratory waveform, exhibiting statistically marginal improvement. This condition is deemed to occur if the final vote during certain pressure control operations equals +1, i.e., x=+1. The four conditions that summarize a patient's response to the pressure, and the final vote value "x" associated with each condition, are given below for this situation:

1) statistically significant degradation, $x \leq -2$
2) statistically no change, $-2 < x < 1$
2.5) statistically marginal improvement, and x=1
3) statistically significant improvement. $x \geq 2$ The following table summarizes where each condition (1), (2), (2.5) or (3) falls for each value of x in this situation:

| x = −4 | x = −3 | x = −2 | x = −1 | x = 0 | x = 1 | x = 2 | x = 3 | x = 4 |
|---|---|---|---|---|---|---|---|---|
| (1) | (1) | (1) |  |  |  |  |  |  |
|  |  |  | (2) | (2) |  |  |  |  |
|  |  |  |  |  | (2.5) |  |  |  |
|  |  |  |  |  |  | (3) | (3) | (3) |

It is to be understood that greater or fewer conditions can be provided depending on how fine tuned the auto-CPAP control layer should be to changes in the patient's condition.

4. Auto-CPAP Control Module

The auto-CPAP controller uses the final voting level described above, which is an indication of the patient's response to the pressure being provided to his or her airway by the pressure support system, along with its current mode of operation, to determine what actions to take. Three general cases are presented below to describe the behavior of the auto-CPAP controller.

a. Case 1—Startup

Figure 26:
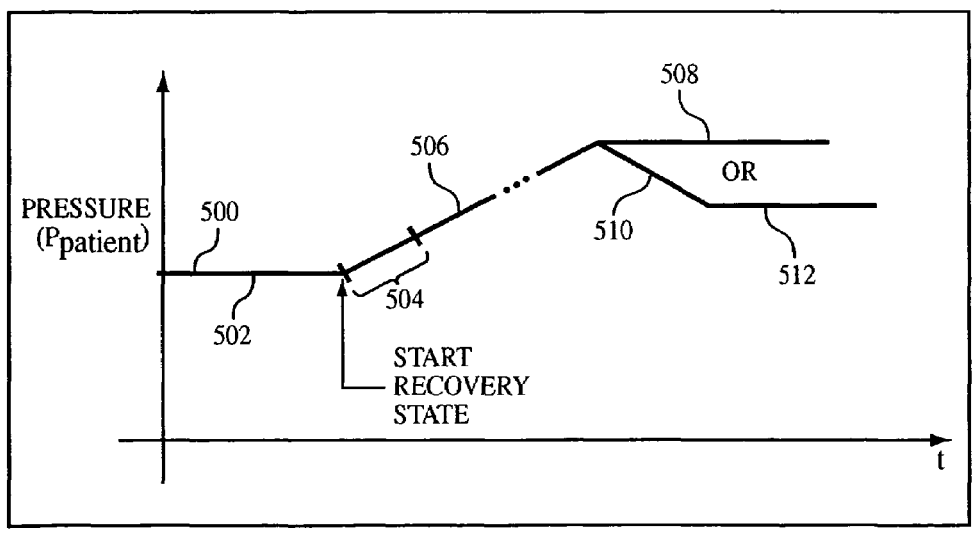
FIG. 26 illustrates an exemplary pressure curve output by the pressure support system during a pressure increase operation.

FIG. 26 illustrates a pressure curve 500 output by the pressure support system during Case 1. When the pressure support system is turned on, it will enter a hold period 502 and collect data. In a preferred embodiment, this hold period lasts 5 minutes. However, the duration of the hold period can be a value other than 5 minutes, so long as enough time elapses to collect a meaningful amount of data. At the end of this period, auto-CPAP controller 354 initiates a recovery state in which the patient pressure is ramped up slowly, with a targeted increase of 1.5 cmH$_2$O, and at a rate of increase of approximately 0.5 cmH$_2$O/min.

During this ramping, the trend data is continually examined by auto-CPAP monitor 352 using the four conditions, (1), (2), (2.5) and (3), to determine if the patient flow profile has experienced statistically significantly degradation—condition (1), statistically no change—condition (2), statistically margin improvement—condition (2.5), or statistically significant improvement—condition (3) during the ramp period. However, no action is taken on this determination until ~2.5 minutes have elapsed since the start of the pressure increase. This 2.5 minute lockout window 504 is provided to allow the system to collect enough data for trending purposes. It can be appreciated that the duration of the lockout interval can vary, for example, between 2–4 minutes. However, the longer this lockout window, the less responsive the system will be to treat any potential breathing disorders.

If the patient's inspiratory flow waveform has improved or degraded during ramp 506, the ramping and trending continues until the improvement or degradation ceases, for example the patient's condition changes from (3) to (2.5) or the patient's condition changes from (1) to (2). Then, a 5-minute hold period will be started, as indicated by pressure curve 508. If there is no improvement during the ramp, i.e., the patient's inspiratory flow profile stays the same—condition (2) or condition (2.5), auto-CPAP controller 354 decreases the pressure 1.5 cmH$_2$O, as indicated by pressure curve 510, and a 5 minute hold period 512 is then started. This sequence of pressure control is intended to determine if flow limitation exists in the waveforms, and to locate an ideal pressure at which flow limitation no longer exists. If flow limitation is detected during any hold period (indicating that the patient may have changed position or sleep stage), the slow ramp up will again be initiated.

b. Case 2—Return from a Higher Priority Controller

During the course of the pressure support therapy, which typically repeats throughout the night, higher level controllers, such as snore controller 144 or apnea/hypopnea controller 168, may temporarily take control and perform pressure changes as discussed above. Once all active high priority controllers are finished, control is returned to auto-CPAP controller 354. Upon receiving control from a higher priority controller, the auto-CPAP controller performs the same actions as described in Case 1 above, with the exception that the initial 5 minute hold period is replaced by a ~3 to 3.5' minute period.

c. Case 3—Patient Pressure Decreases

Figure 27A:
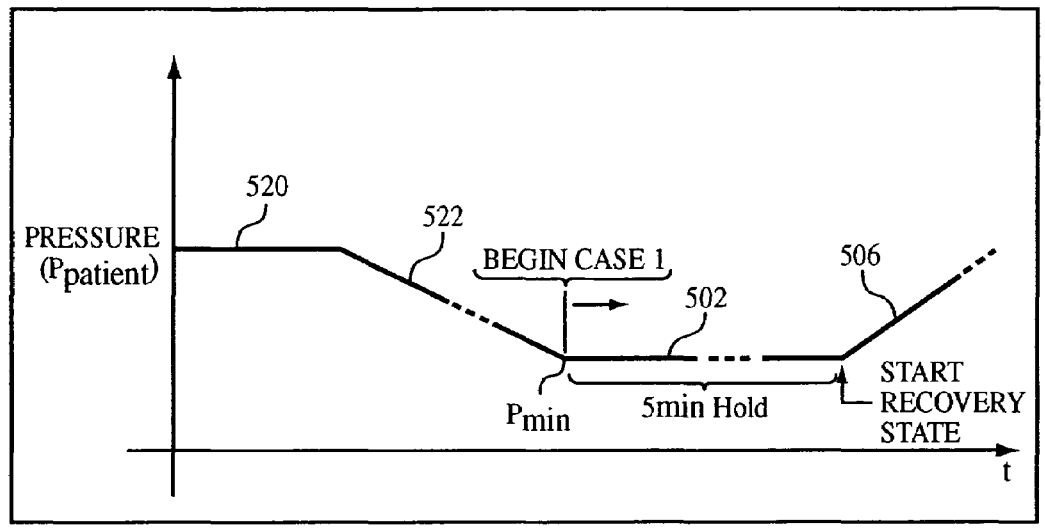
FIGS. 27A and 27B illustrate further exemplary pressure curves output by the pressure support system of the present invention.
Figure 27B:
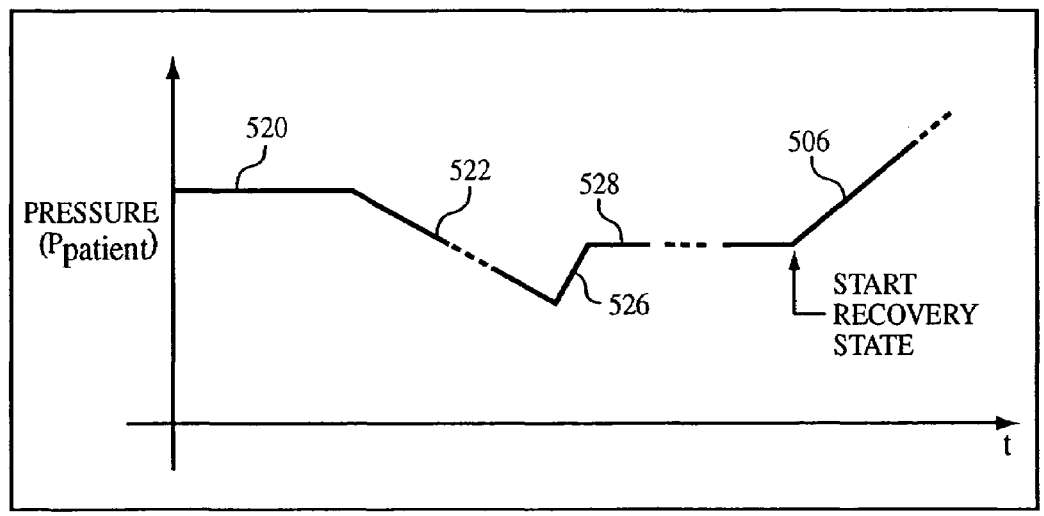

When the last 5-minute hold period from either Case 1 or Case 2 is completed, as indicated by pressure curve 520 in FIGS. 27A and 27B, the next search sequence is started. In this search sequence, the pressure delivered by the system is slowly lowered at a rate of 0.5 cmH$_2$O/minute, as indicated by curve 522. Prior to starting the decrease in pressure, the breath measure trends are initialized with up to the last three minutes of available data.

After ramping down 0.5 cmH$_2$O, the trend data is then continually examined to determine if the patient inspiratory flow profile has degraded or not over the ramp period. In this trend analysis, only the three patient conditions (1), (2) and (3) are taken into consideration. If there is no patient flow profile degradation detected (condition (2)), the ramp and trending will continue until the minimum system pressure P$_{min}$ is reached as shown in FIG. 27A. Thereafter, auto-CPAP controller 354 begins the Case 1 pressure control discussed above and begins a 5 minute hold period 502.

If, during the pressure decrease, the patient inspiratory flow profile has degraded, for example, moved from condition (2) to condition (1), the patient pressure will be quickly increased 1.5 cmH$_2$O, curve 526, and then held constant for up to 10 minutes, curve 528. See FIG. 27B. Once the 10 minute hold period ends, auto-CPAP controller 354 directly enters the recovery state discussed above with respect to Case 1, and initiates pressure increase 506.

This entire sequence is intended to determine the pressure at which flow limitation occurs and then raise the pressure to an ideal setting. This sequence is repeated throughout the night to locate the optimal pressure as patient conditions change and to improve comfort by keeping the pressure as low as practical. If flow limitation is detected during any hold period (indicating that the patient may have changed position or sleep stage), the slow ramp up (recovery state) will again be initiated.

During this pressure decrease, where the auto-CPAP controller is searching for a potential flow limitation point, the chance of a snore occurring is increased. For this reason, the present invention contemplates reducing the required number of snore events from three to two that will cause snore monitoring module 142 to request that the snore controller take control. This effectively increases the system's sensitivity to snore during the pressure decrease interval.

During any hold period, such as hold period 502, 508, 512, 520, or 528, auto-CPAP controller 354 can enter the recovery state discussed above in Case 1 to attempt to provide the optimal pressure to the patient. This may occur, for example, if the trends data analyzed during the hold indicated that the patient's inspiratory waveform profile is experiencing a statistically significant degradation (condition (1)).

J. Detection of Central Versus Obstructive Apnea/Hypopnea Events

In Section G above, in which the operation of the apnea/hypopnea control layer is discussed, it was noted that A/H detection module 164 cannot detect the difference between obstructive apnea/hypopnea events and central apnea/hypopnea events but compensates for this shortcoming by the manner in which the pressure is delivered to the patient. However, a further embodiment of the present invention contemplates detecting the difference between obstructive apnea/hypopnea events and central apnea/hypopnea events A/H via detection module 164. This is accomplished, for example, by monitoring the patient's inspiratory waveform during the apnea/hypopnea period, immediately after the end of the apnea/hypopnea period, or during both these periods as discussed below.

If it is determined that the patient is experiencing an obstructive apnea/hypopnea event, the pressure is delivered to the patient as discussed above in Section G. If, however, the patient is experiencing a central apnea/hypopnea event, it is preferable not to increase the pressure. It is generally recognized that increasing the pressure delivered to the patient does not treat an episode of central apnea/hypopnea. Therefore, the present invention contemplates maintaining the pressure delivered to the patient at the current level or even decreasing the pressure if the patient is deemed to be experiencing a central apnea/hypopnea.

Maintaining the pressure at its current level is accomplished, according to one embodiment of the present invention, by causing the A/H detection module to reject the apnea/hypopnea event as an apnea/hypopnea event if it is determined to be a central apnea/hypopnea event. In which case, the system acts as if no apnea/hypopnea event was detected and does not request that A/H controller 168 take control of the system. The present invention also contemplates reducing the pressure delivered to the patient if it is determined that the patient is experiencing a central apnea.

Figure 28:
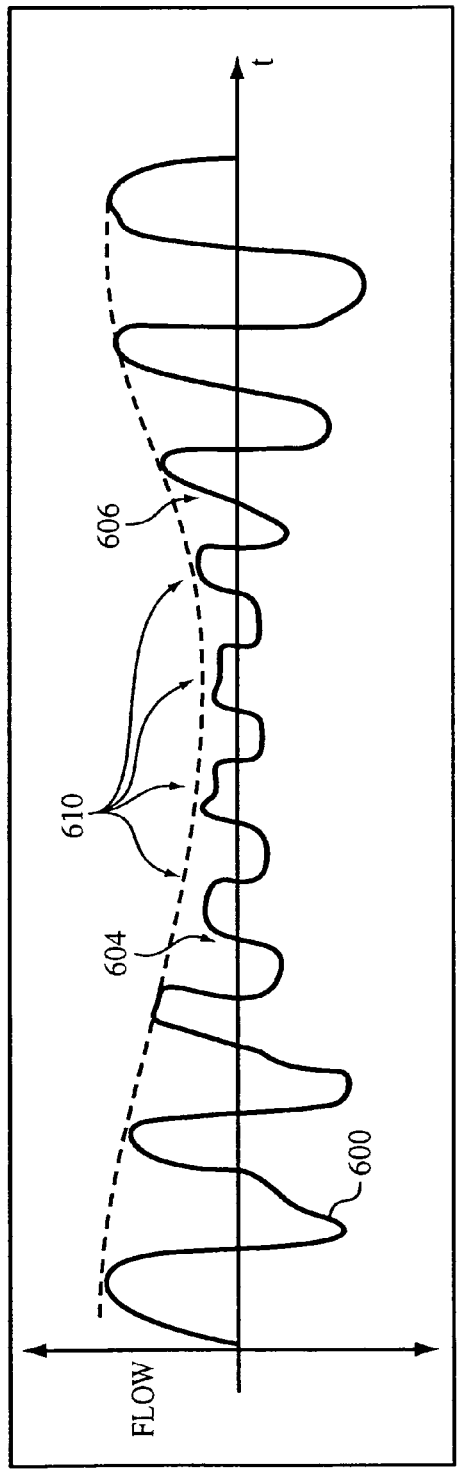
FIG. 28 illustrates an exemplary patient flow waveform during an obstructive/restrictive apnea/hypopnea event.
Figure 29:
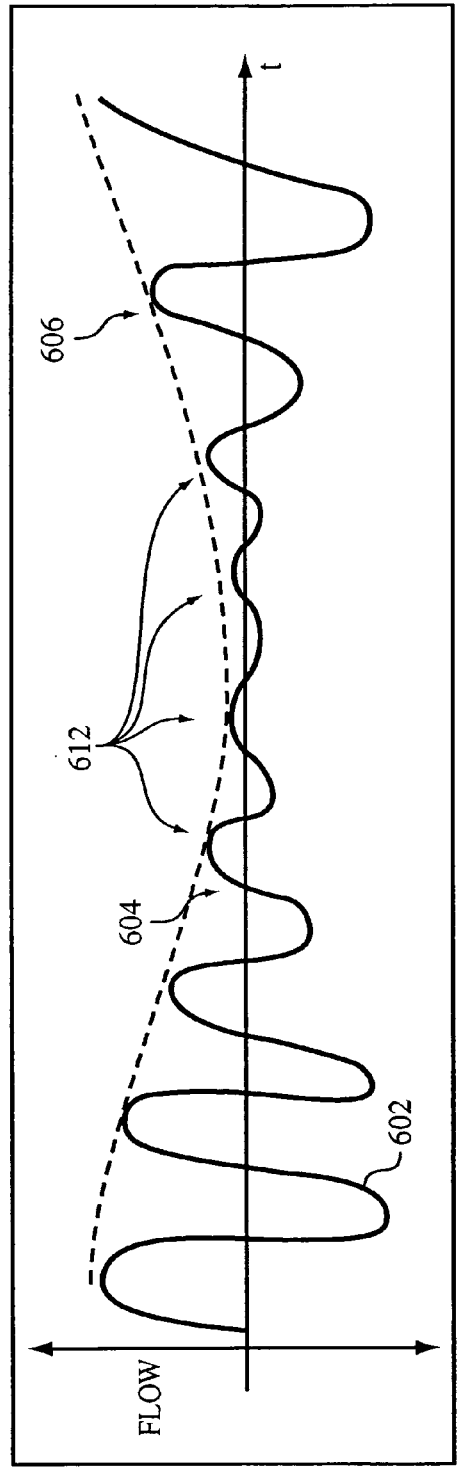
FIG. 29 illustrates an exemplary patient flow waveform during a central apnea/hypopnea event.
Figure 30:
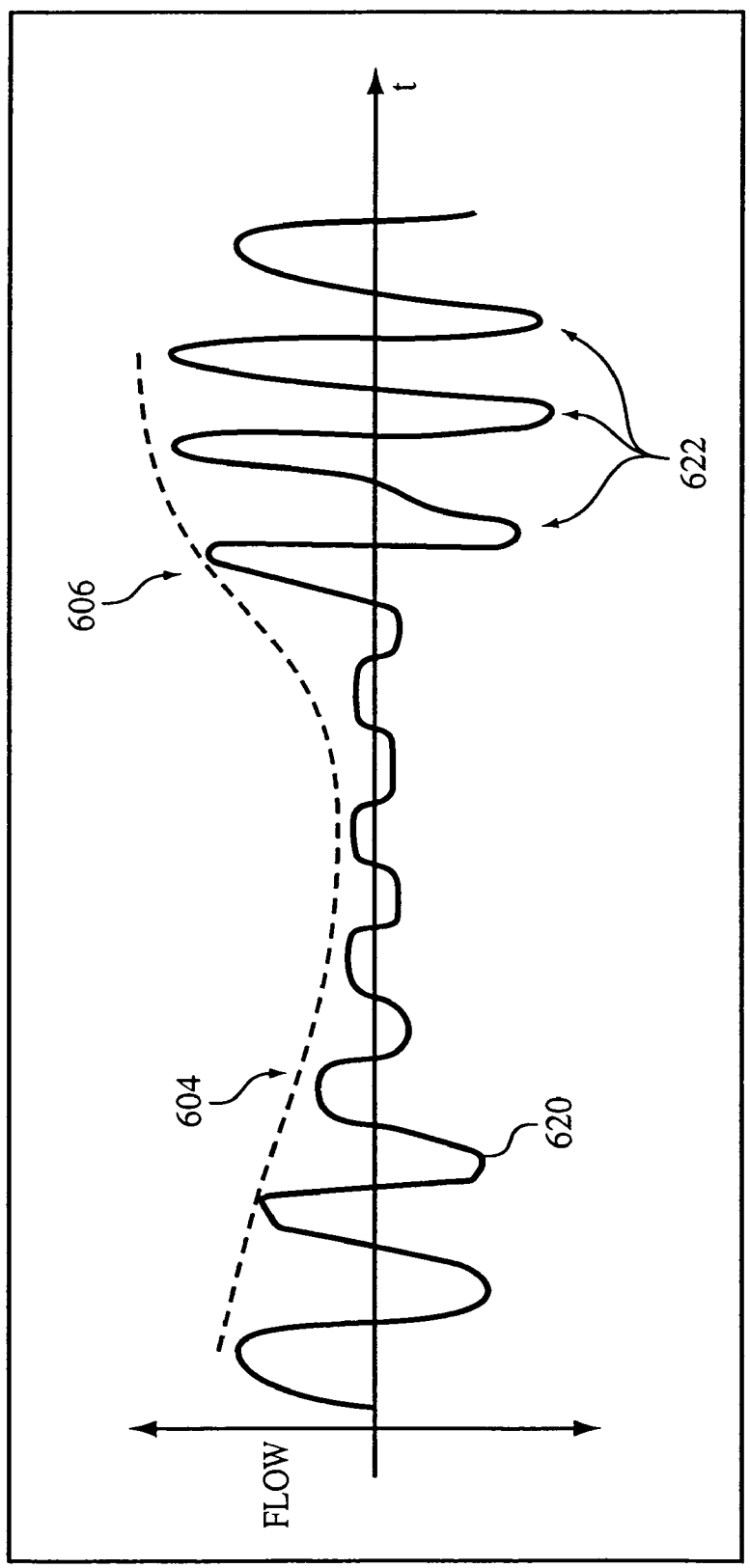
FIG. 30 illustrates a further exemplary patient flow waveform during an obstructive/restrictive apnea/hypopnea event.

The manner in which the present invention discriminates between obstructive/restrictive apnea/hypopnea events and central apnea/hypopnea events is discussed below with reference to FIGS. 28–30, which illustrate exemplary patient flow waveforms during an obstructive/restrictive apnea/hypopnea events (FIGS. 28 and 30) and during a central apnea/hypopnea event (FIG. 29). The determination of whether the patient is experiencing an obstructive/restrictive apnea/hypopnea event or a central apnea/hypopnea event is preferably made by A/H detection module 164, which supplies its determination to A/H monitoring module 166 to actuate A/H controller 168 so that the appropriate pressure control can be made as discussed above.

In a presently preferred exemplary embodiment, the patient's inspiratory waveform during the apnea/hypopnea period is monitored to determine whether he or she is experiencing an obstructive/restrictive apnea/hypopnea event or a central apnea/hypopnea event. In the hypothetical patient flow waveforms 600 and 602 in FIGS. 28 and 29, respectively, the apnea/hypopnea event begins at point 604 and terminates at point 606, which is determined as discussed above in Sections G(3) and G(4). It should be noted that waveforms 600 and 602 are provided to illustrate a technique used by an exemplary embodiment of the present invention to determine whether the patient is experiencing an obstructive/restrictive apnea/hypopnea event or a central apnea/hypopnea event. These waveforms may not be to scale and may not accurately represent an actual patient flow. The dashed lines in FIGS. 28 and 29 illustrate the patient flow valley that occurs during an apnea/hypopnea event. It is in this valley or apnea/hypopnea period that the present invention examines the shape of the patient's flow to determine whether he or she is experiencing an obstructive/restrictive apnea/hypopnea event or a central apnea/hypopnea event.

More specifically, the present inventors understood that during an obstructive/restrictive apnea/hypopnea event, the shape characteristics of the patient's inspiratory waveform tends to exhibit the same shape characteristics associated with a restricted airflow. Namely, during an obstructive/restrictive apnea/hypopnea event, the waveform exhibits an increase in flatness (becomes flatter), a decrease in roundness (becomes less round), an increased skewness (becomes more skewed)(as shown in FIG. 22) or any combination of these characteristics.

For example, in FIG. 28 inspiratory waveforms 610 occurring during the apnea/hypopnea period between points 604 and 606 tend to have an increased degree of flatness, a lack of roundness, an increased skewness, or any combination of these characteristics, indicating that waveform 600 represents an obstructive/restrictive apnea/hypopnea rather than a central apnea/hypopnea. In FIG. 29, on the other hand, inspiratory waveforms 612 occurring during the apnea/hypopnea period between points 604 and 606 tend to have no increased degree of flatness, relatively normal roundness, and no increase in skewness, indicating that waveform 602 represents a central apnea/hypopnea rather than a central apnea/hypopnea. Thus, the present invention contemplates monitoring the flatness, roundness and skewness of the waveforms occurring during the apnea/hypopnea period via A/H detection module 164 to determine whether the patient is experiencing an obstructive/restrictive apnea/hypopnea event or a central apnea/hypopnea event. In a presently preferred embodiment, all of these shape criteria are monitored during the apnea/hypopnea period. It is to be understood that the present invention contemplates monitoring as few as one criteria, such as flatness, to make this determination.

In a second embodiment of the present invention, the patient's airflow waveform during a period immediately after the end of the apnea/hypopnea is monitored to determine whether he or she experienced an obstructive/restrictive apnea/hypopnea event or a central apnea/hypopnea event. More specifically, the present inventors understood that the patient's respiratory flow is different at the end of the apnea/hypopnea event depending on whether the patient suffered an obstructive/restrictive apnea/hypopnea or a central apnea/hypopnea. More specifically, as shown in FIG. 30, which depicts a patient's respiratory flow waveform 620 during an obstructive/restrictive apnea/hypopnea event, it has been determined that at the termination of an obstructive apnea/hypopnea event, a patient often tends to take a relatively large gasping breath or series of gasping breaths, generally indicated as breaths 622 in FIG. 30. At the end of a central apnea/hypopnea event, on the other hand, the patient does not tend to take large breaths. See FIG. 29.

Thus, the present invention contemplates determining whether the patient has experienced an obstructive/restrictive apnea/hypopnea event or a central apnea/hypopnea event by determining whether the patient has taken large gasping breaths at the end of the apnea/hypopnea. This is accomplished, for example, by the tidal volume of the breaths immediately following the end of the apnea/hypopnea period and comparing this volume against a predetermined threshold volume. If the breaths have a tidal volume that exceeds the threshold level, the patient is deemed to have experienced an obstructive/restrictive apnea/hypopnea. In which case, the pressure is delivered to the patient as discussed above in Section G.

It should be noted that the present invention contemplates monitoring respiratory characteristics other than tidal volume in order to determine whether the patient is taking large, gasping breaths at the end of the apnea/hypopnea period. For example, the peak flow can also be measured against a threshold to evaluate whether the patient is taking relatively large breaths.

Two techniques have been discussed above for determining whether a patient is experiencing an obstructive/restrictive apnea/hypopnea event or a central apnea/hypopnea event. These techniques can be used alone or in combination to make this determination. Furthermore, the present invention also contemplates using any conventional technique for detecting a central apnea, either alone or in combination with the two techniques discussed above, such as monitoring for cardiogenic respiratory events or testing the airway for patency during an apnea/hypopnea period.

In a presently preferred embodiment, the A/H control layer does not discriminate between obstructive/restrictive and central apnea/hypopnea event unless the pressure being delivered to the patient is above a certain threshold. This threshold ensures that a pressure treatment is provided if the patient is being treated with a relatively low pressure regardless of whether the apnea/hypopnea was central or obstructive. If the pressure is below this threshold, the system performs the pressure treatment as discussed above in Section G. If, however, the patient is being treated with a relatively high pressure, i.e., a pressure above the pressure threshold, it is preferable to determine whether the apnea/hypopnea is central or obstructive, because, as noted above, increasing the pressure for a central apnea provided no therapeutic effect.

In a preferred embodiment, the pressure threshold is set at 8 cmH$_2$O, which has been determined from analysis of clinical data to be a pressure level that provides a moderate degree of pressure support for most patients, but is not too high as to cause unduly high pressures to be delivered should the patient be experiencing a central apnea/hypopnea. It is to be understood that this threshold can have other values and can be adjustable depending on the characteristics of the patient or the patient's history.

K. Conclusion

It can be appreciated that the present invention contemplates providing additional control layers to those shown in FIG. 2. Likewise one or more of the control layers shown in FIG. 2 can be deleted depending on the desired operating capability of the pressure support system. Furthermore, the present invention is not intended to be limited to the prioritization hierarchy shown in FIG. 2. For example, the apnea/hypopnea control layer (priority #6) can be given a higher priority by interchanging it with the big leak control layer (priority #5).

With reference to FIG. 2, request processor 106 resets detection modules 102, monitoring modules 104, and control modules 100 generally based on changes between control modules. Detection modules 102 are generally only reset by machine based control layers above line 108. Monitoring modules 104 are generally reset after a control layer completes its pressure treatment and has given control of the pressure support system back to the lower control layers. This is done so that the monitors can keep track of the patient's progress since the last pressure treatment. This is also important in order to avoid over-treating the patient in a situation where two overlapping patient events occur, e.g., hypopnea with snoring. If the snore controller is actively treating the snoring condition, and, thus, is indirectly aiding in the treatment of the simultaneously occurring hypopnea, the hypopnea monitor will be reset, thus, inhibiting an additional follow-on request from the hypopnea monitor. Control modules 100 are reset based on the priority of the current control layer. When the current controller gives control of the pressure support system back to the lower control layers, generally all lower control layers are reset so that their processing will start over from where the last control layer left off.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims.

What is claimed is:

1. An auto-titration pressure support system comprising:
a pressure generating system adapted to generate a flow of breathing gas at a selectable pressure level;
a patient circuit having a first end adapted to be coupled to the pressure generating system and a second end adapted to be coupled to an airway of a patient;
a monitoring system associated with the patient circuit or the pressure generating system and adapted to measure a parameter indicative of a pressure at a patient's airway, a flow of gas in such a patient's airway, or both and to output a pressure signal, a flow signal indicative thereof, respectively, or both; and
a controller coupled to the monitoring system and the pressure generating system, for controlling a pressure of the flow of breathing gas output by the pressure generating system based on the output of the monitoring system, wherein the controller is programmed to operate according to one control layer in a set of prioritized control layers, wherein each control layer in the set of prioritized control layers competes for control of the pressure generating system with the other control layers, and wherein each control layer implements a unique pressure control process for controlling the pressure of the flow of breathing gas output by the pressure generating system.

2. The system of claim 1, wherein each control layer in the set of prioritized control layer includes:
a detection module that receives the pressure signal, the flow signal or both;
a monitoring module that monitors an output of the detection module to determine whether to request that the control layer take control of the pressure generating system; and
a control module that control the operation of the pressure generating system responsive to the control layer being granted control thereof.

3. The system of claim 1, wherein the set of prioritized control layers include:
(a) flow limit control layer that monitors the flow signal to determine whether the pressure generating system is exhibiting a large leak indicative of the patient circuit not being connected to an airway of a patient, and causes the pressure generating system to lower the pressure of the flow of breathing gas responsive to detection of the large leak and maintains the pressure generating system at the lower pressure;
(b) snore control layer that monitors the flow signal, the pressure signal, or both for snoring, and causes the pressure generating system to increase the pressure of the flow of breathing gas responsive to detection of snore;
(c) a big leak control layer that monitors the flow signal to determine whether the pressure generating system is exhibiting a leak that is less than the large leak but great enough to cause the pressure support system to not operate reliably, and causes the pressure generating system to lower the pressure of the flow of breathing gas responsive to detection of the large leak for predetermined period of time;
(d) an apnea/hypopnea control layer that monitors the flow signal, the pressure signal, or both to determine whether the patient is experiencing an apnea, a hypopnea, or both, and causes the pressure generating system to adjust the pressure of the flow of breathing gas responsive to detection of apnea, hypopnea or both;
(e) a variable breathing control layer that monitors the flow signal to determine whether the patient is experiencing erratic breathing, and causes the pressure generating system to adjust the pressure of the flow of breathing gas responsive to detection of erratic breathing; and
(f) an auto-CPAP control layer that controls the pressure of the flow of breathing gas responsive to proactively search for a pressure that optimizes the pressure provided to the patient to treat disordered breathing.

4. The system of claim 3, wherein:
(1) the flow limit control layer has a higher priority than the snore control layer, the big leak control layer, the apnea/hypopnea control layer, the variable breathing control layer, and the auto-CPAP control layer;
(2) the snore control layer has a higher priority than the big leak control layer, the apnea/hypopnea control layer, the variable breathing control layer, and the auto-CPAP control layer and has a lower priority than the flow limit control layer;
(3) the big leak control layer has a higher priority than the apnea/hypopnea control layer, the variable breathing control layer, and the auto-CPAP control layer and has a lower priority than the flow limit control layer and the snore control layer;
(4) the apnea/hypopnea control layer has a higher priority than the variable breathing control layer, and the auto-CPAP control layer and has a lower priority than the flow limit control layer, the snore control layer and the big leak control layer; and
(5) the variable breathing control layer has a higher priority than the auto-CPAP control layer and has a lower priority than the flow limit control layer, the snore control layer, the big leak control layer, and the apnea/hypopnea control layer.

5. The system of claim 1, further comprising a manual input for controlling the operation of the pressure support system, and wherein the set of prioritized control layers include at least one first control layer that is initiated based on the manual input and at least one second control layer that is initiated based on the pressure signal, the flow signal or both, wherein the at least one first control layer has a higher priority than the at least one second control layer.

6. The system of claim 5, wherein the first control layer is a ramp control layer that causes the pressure generating system to gradually increase the pressure of the flow of breathing gas from a relatively low level to a target level responsive to receipt of a ramp activation signal as the manual input.

7. The system of claim 6, wherein the second control layer includes at least one of the following control layers:
   (a) flow limit control layer that monitors the flow signal to determine whether the pressure generating system is exhibiting a large leak indicative of the patient circuit not being connected to an airway of a patient, and causes the pressure generating system to lower the pressure of the flow of breathing gas responsive to detection of the large leak and maintains the pressure generating system at the lower pressure;
   (b) snore control layer that monitors the flow signal, the pressure signal, or both for snoring, and causes the pressure generating system to increase the pressure of the flow of breathing gas responsive to detection of snore;
   (c) a big leak control layer that monitors the flow signal to determine whether the pressure generating system is exhibiting a leak that is less than the large leak but great enough to cause the pressure support system to not operate reliably, and causes the pressure generating system to lower the pressure of the flow of breathing gas responsive to detection of the large leak for predetermined period of time;
   (d) an apnea/hypopnea control layer that monitors the flow signal, the pressure signal, or both to determine whether the patient is experiencing an apnea, a hypopnea, or both, and causes the pressure generating system to adjust the pressure of the flow of breathing gas responsive to detection of apnea, hypopnea or both;
   (e) a variable breathing control layer that monitors the flow signal to determine whether the patient is experiencing erratic breathing, and causes the pressure generating system to adjust the pressure of the flow of breathing gas responsive to detection of erratic breathing; and
   (f) an auto-CPAP control layer that controls the pressure of the flow of breathing gas responsive to actively search for a pressure that optimizes the pressure provided to the patient to treat disordered breathing.

8. An auto-titration pressure support system comprising:
a pressure generating system adapted to generate a flow of breathing gas at a selectable pressure level;
a patient circuit having a first end adapted to be coupled to the pressure generating system and a second end adapted to be coupled to an airway of a patient;
a monitoring system associated with the patient circuit or the pressure generating system and adapted to measure a parameter indicative of a flow of gas in such a patient's airway and to output a flow signal indicative thereof; and
a controller coupled to the monitoring system and the pressure generating system, for controlling the pressure generating system based on the output of the monitoring system, wherein the controller determines a breathing parameter from the flow signal, wherein the controller analyzes a variability of the breathing parameter and controls the pressure generating system based on a result of the variability analysis, and wherein analyzing the variability of the breathing parameter includes calculating a weighted peak flow and a best-fit trend line for the weighted peak flow over a plurality of breathing cycles, and calculating a variable breathing number (VB#) as follows:

$$VB\# = \frac{\text{standard deviation}}{\text{adjusted mean flow}},$$

wherein the standard deviation is calculated as a standard deviation of the weighted peak flows over a plurality of breathing cycles from the best-fit trend line, and wherein the adjusted mean flow is determined based on an actual patient flow determined from the flow signal.

9. The system of claim 8, wherein a relationship between the adjusted mean flow and the actual patient flow varies based on the flow signal.

10. The system of claim 8, wherein the controller compares the variable breathing number to a first threshold and causes the pressure generating system to control the pressure of the flow of breathing gas as follows responsive to the variable breathing number exceeding the first threshold:
   (1) maintain the pressure at a constant level if the pressure of the flow of breathing gas was not increasing or decreasing when variability of the breathing parameter is detected;
   (2) decrease the pressure if the pressure of the flow of breathing gas was increasing when variability of the breathing parameter is detected; and
   (3) increase the pressure if the pressure of the flow of breathing gas was decreasing when variability of the breathing parameter is detected.

11. An auto-titration pressure support system comprising:
a pressure generating system adapted to generate a flow of breathing gas at a selectable pressure level;
a patient circuit having a first end adapted to be coupled to the pressure generating system and a second end adapted to be coupled to an airway of a patient;
a monitoring system associated with the patient circuit or the pressure generating system and adapted to measure a parameter indicative of a flow of gas in such a patient's airway and to output a flow signal indicative thereof; and
a controller coupled to the monitoring system and the pressure generating system, for controlling the pressure generating system based on the output of the monitoring system,
wherein the controller determines a skewness of a patient's inspiratory waveforms from the output of the flow sensor and controls the pressure generating system according to the skewness determination, and wherein the controller determines the skewness of the inspiratory waveform by segmenting the inspiratory waveform into a first region that corresponds to a beginning portion of the inspiratory waveform and a second region that corresponds to a middle portion of the inspiratory waveform, and comparing the flow in the second region to the flow in the first region.

12. The system of claim 11, wherein the flow in the first region corresponds to an average of the highest rates of flow in the first region, and wherein the flow in the second region corresponds to an average of the highest rates of flow in the second region.

13. The system of claim 11, wherein the first region corresponds to approximately a first third of the inspiratory waveform and the second region corresponds to approximately a second third of the inspiratory waveform, and wherein the highest flow rates in the first region and the second region are defined as the flow rates within 5% of the highest flow rates in each region.

14. The system of claim 11, wherein the skewness is calculated as a skewness number follows:

$$\text{skewness number} = \frac{\text{Average of the highest flow rates in the second region}}{\text{Average of the highest flow rates in the first region}}.$$

15. The system of claim 14, wherein the controller causes the pressure generating system to increase the pressure of the flow of breathing gas responsive to a decrease in the skewness number.

16. An auto-titration pressure support system comprising:
a pressure generating system adapted to generate a flow of breathing gas at a selectable pressure level;
a patient circuit having a first end adapted to be coupled to the pressure generating system and a second end adapted to be coupled to an airway of a patient;
a monitoring system associated with the patient circuit or the pressure generating system and adapted to measure a parameter indicative of a flow of gas in such a patient's airway and to output a flow signal indicative thereof; and
a controller coupled to the monitoring system and the pressure generating system, for controlling the pressure generating system based on the output of the monitoring system, wherein the controller is programmed determine whether the patient is experiencing a central apnea/hypopnea or an obstructive/restrictive apnea/hypopnea by monitoring one or more of the following: (1) at least one shape parameter associated with the flow of gas during an apnea/hypopnea period, and (2) a characteristic of the flow of gas at the end of the apnea/hypopnea period indicative of an increase in respiratory effort, wherein the shape parameters monitored by the controller during an apnea/hypopnea period include a flatness of an inspiratory portion of a flow waveform, a roundness of the inspiratory portion of the flow waveform, a skewness of the inspiratory portion of the flow waveform, and wherein the controller considers a patient to be experiencing an obstructive/restrictive apnea/hypopnea responsive to the inspiratory portion of the flow waveform exhibiting at least one of an increase in flatness, a decrease in roundness, and an increased skewness, otherwise the controller considers the patient to be experiencing a central apnea/hypopnea, and wherein the controller prevents a pressure increase by the pressure generating system responsive to a determination that the patient is experiencing a central apnea/hypopnea.

17. The system of claim 16, wherein the characteristic of the flow of gas at the end of the apnea/hypopnea period is a volume or a peak flow related characteristic, wherein the controller considers a patient to be experiencing an obstructive/restrictive apnea/hypopnea responsive to the volume or the peak flow related characteristic at the end of the apnea/hypopnea period exceeding a predetermined threshold, otherwise the controller considers the patient to be experiencing a central apnea/hypopnea, and wherein the controller prevents a pressure increases by the pressure generating system responsive to a determination that the patient is experiencing a central apnea/hypopnea.

18. An auto-titration pressure support system comprising:
a pressure generating system adapted to generate a flow of breathing gas at a selectable pressure level;
a patient circuit having a first end adapted to be coupled to the pressure generating system and a second end adapted to be coupled to an airway of a patient;
a monitoring system associated with the patient circuit or the pressure generating system and adapted to measure a parameter indicative of a pressure at a patient's airway, a flow of gas in such a patient's airway, or both and to output a pressure signal, a flow signal indicative thereof, respectively, or both; and
a controller coupled to the monitoring system and the pressure generating system, for controlling the pressure generating system based on the output of the monitoring system, wherein the controller is programmed to:
(1) determine whether the patient is experiencing an apnea/hypopnea based on the pressure signal or the flow signal,
(2) set a pressure treatment limit based on a pressure at a time an apnea/hypopnea is detected,
(3) cause the pressure generating system to increase a pressure of the flow of breathing gas delivered to a patient responsive to a current pressure being below the pressure treatment limit, and
(4) cause the pressure generating system to decrease a pressure of the flow of breathing gas delivered to a patient responsive to a current pressure being at or above the pressure treatment limit.

* * * * *